United States Patent [19]
Brendel et al.

[11] Patent Number: 6,008,245
[45] Date of Patent: Dec. 28, 1999

[54] SULFONAMIDE-SUBSTITUTED BENZOPYRAN DERIVATIVES, PROCESSES FOR THEIR PREPARATION, THEIR USE AS A MEDICAMENT, AND PHARMACEUTICAL PREPARATIONS COMPRISING THEM

[75] Inventors: Joachim Brendel, Bad Vilbel; Uwe Gerlach, Hattersheim; Hans Jochen Lang, Hofheim; Klaus Weidmann, Kronberg, all of Germany

[73] Assignee: Hoechst Marion Roussel Deutschland GmbH, Frankfurt am Main, Germany

[21] Appl. No.: 09/184,110

[22] Filed: Nov. 2, 1998

[30] Foreign Application Priority Data

Nov. 3, 1997 [DE] Germany .................. 197 48 469

[51] Int. Cl.$^6$ .................. A61K 31/35; C07D 311/04
[52] U.S. Cl. .................. 514/456; 549/398; 549/399; 549/404
[58] Field of Search .................. 514/456; 549/398, 549/399, 404

[56] References Cited

FOREIGN PATENT DOCUMENTS

A-0 315 009  5/1989  European Pat. Off. .
A-0 389 861  10/1990  European Pat. Off. .
1-294677  11/1989  Japan .

*Primary Examiner*—Joseph K. McKane
*Assistant Examiner*—Joseph Murray
*Attorney, Agent, or Firm*—Finnegan, Henderson, Farabow, Garrett & Dunner, L.L.P.

[57] ABSTRACT

Sulfonamide-substituted benzopyran derivatives, processes for their preparation, their use as a medicament, and pharmaceutical preparations comprising them Compounds of the formula I

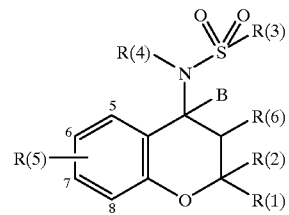

having the meanings of the substituents indicated in the claims are outstandingly active substances for the production of medicaments for the prophylaxis and for the therapy of cardiovascular disorders, in particular arrhythmias, for the treatment of ulcers of the gastrointestinal region or for the treatment of diarrheal diseases.

43 Claims, No Drawings

SULFONAMIDE-SUBSTITUTED BENZOPYRAN DERIVATIVES, PROCESSES FOR THEIR PREPARATION, THEIR USE AS A MEDICAMENT, AND PHARMACEUTICAL PREPARATIONS COMPRISING THEM

Sulfonamide-substituted benzopyran derivatives, processes for their preparation, their use as a medicament, and pharmaceutical preparations comprising them The invention relates to compounds of the formula I

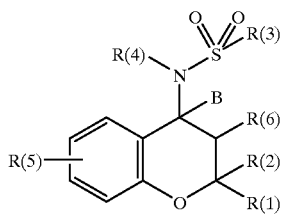

I in which R(1), R(2), R(3), R(4), R(5), R(6) and B have the meanings indicated in the following, their preparation and their use, in particular in pharmaceuticals. The compounds affect the potassium channel opened by cyclic adenosine monophosphate (cAMP) or the $I_{Ks}$ channel and are outstandingly suitable as pharmaceutically active compounds, for example for the prophylaxis and therapy of cardiovascular disorders, in particular arrhythmias, for the treatment of ulcers of the gastrointestinal region or for the treatment of diarrheal diseases.

In pharmaceutical chemistry, the 4-acylaminochroman derivatives class has been worked on intensively in recent years. The most prominent representative of this group is cromakalim of the formula A (J. Med. Chem. 1986, 29, 2194).

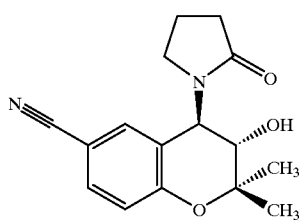

A

Cromakalim and other related 4-acylaminochroman derivatives are compounds having a relaxant action on smooth muscular organs, so that they are used for lowering raised blood pressure as a result of vascular muscle relaxation and in the treatment of asthma as a result of the relaxation of the smooth musculature of the airways. It is common to all these preparations that they act at the cellular level, for example, of smooth muscle cells and lead there to an opening of specific ATP-sensitive $K^+$ channels. The increase in negative charge in the cell (hyperpolarization) induced by the efflux of $K^+$ ions counteracts, via secondary mechanisms, the increase in the intracellular $Ca^{2+}$ concentration and thus cell activation which leads, for example, to muscle contraction.

The compounds of the formula I according to the invention differ structurally from these acylamino derivatives, inter alia, by the replacement of the acylamino group by a sulfonylamino function. While cromakalim (formula A) and analogous acylamino compounds act as openers of ATP-sensitive $K^+$ channels, the compounds of the formula I according to the invention having the sulfonylamino structure, however, do not show any opening action on this $K^+$ (ATP) channel, but surprisingly show a strong and specific blocking (closing) action on a $K^+$ channel which is opened by cyclic adenosine monophosphate (cAMP) and differs fundamentally from the $K^+$ (ATP) channel mentioned. More recent investigations show that this $K^+$ (cAMP) channel identified in colonic tissue is very similar, perhaps even identical, to the $I_{Ks}$ channel identified in the cardiac muscle. In fact, it was possible, for the compounds of the formula I according to the invention, to show a strong blocking action on the $I_{Ks}$ channel in guinea-pig cardiomyocytes and on the $I_{sK}$ channel expressed in Xenopus oocytes. As a result of this blocking of the $K^+$ (cAMP) channel or of the $I_{Ks}$ channel, the compounds according to the invention display pharmacological actions of high therapeutic utility in the living body.

In addition to the abovementioned cromakalim and acylaminochroman derivatives, compounds having 4-sulfonylaminochroman structure are described in the literature. EP-A-389 861 and JP 01294677 describe 3-hydroxychroman and chromen derivatives having a cyclic 4-sulfonylamino group (for example compound B), respectively, which are said to act as antihypertensive agents via an activation of the $K^+$ (ATP) channel. The claims of the just-mentioned EP-A-389 861 also embrace compounds having non-cyclic 4-sulfonylamino radicals which are similar to the compounds described in the present invention, but which differ from these in the meaning of R(5). Surprisingly, it has now been found that in particular the substituents for R(5) described in the present application, especially alkoxy, for example butoxy or 4,4,4-trifluorobutoxy, offer considerable advantages compared to compounds having the radicals listed in EP-A-389 861, in particular in the potency for blocking the $I_{Ks}$ channel. The analogous compounds, which are claimed by the authors of EP-A-389 861 but not supported by examples also have an effect on the $I_{Ks}$ channel; however, this effect is less pronounced and was not noticed by the authors of this application. Even if the authors mention, inter alia, a use for the treatment of arrhythmias, it has to be said that the compounds described therein, which are said to effect the opening of the $K^+$ (ATP) channel, should shorten the repolarization time by opening this channel and should therefore rather have proarrhythmic action. In this context, reference should be made to a seminal publication by Lucchesi et al. (J. Cardiovasc. Pharmacol. 15, 1990, 452) in which it was shown in an impressive manner that $K^+$ (ATP) channel openers do not have antiarrhythmic action on the hypoxemic diseased heart or in the case of sudden ischemias, but in contrast cause life-threatening profibrillatory effects.

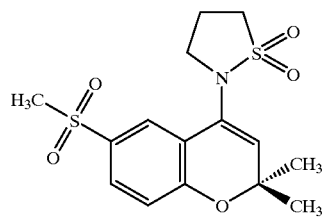

B

In addition to the abovementioned compounds having 4-sulfonylaminochroman structure, some other compounds are known, but these differ both in the structure and in the biological activity significantly from the compounds of the formula I according to the invention. Thus, EP-A-315 009 describes chroman derivatives having 4-phenylsulfonylamino structure which have antithrombotic and antiallergic properties. EP-A-370 901 describes 3-hydroxychroman and chromen derivatives having a 4-sulfonylamino group, where the remaining valency of the nitrogen atom carries a hydrogen atom, which act on the CNS. Further 4-sulfonylaminochroman derivatives are described in Bioorg. Med. Chem. Lett. 4 (1994), 769–773: "N-sulfonamides of benzopyran-related potassium channel openers: conversion of glyburyde insensitive smooth muscle relaxants to potent smooth muscle contractors" and also in FEBS Letters 396 (1996), 271–275: "Specific blockade of slowly activating $I_{sK}$ channels by chromanols . . . " and Pflügers Arch.—Eur. J. Physiol. 429 (1995), 517–530: "A new class of inhibitors of cAMP-mediated Cl-secretion in rabbit colon, acting by the reduction of cAMP-activated $K^+$ conductance".

The present invention relates to compounds of the formula I

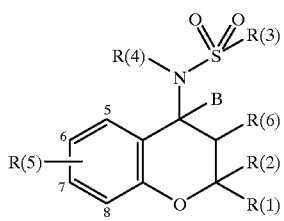

in which R(5) is attached to one of the positions labeled 5, 6, 7 and 8 and in which:

R(1) and R(2)
independently of one another are hydrogen, $CF_3$, $C_2F_5$, $C_3F_7$, alkyl having 1, 2, 3, 4, 5 or 6 carbon atoms or phenyl,
which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino; or R(1) and R(2)
together are an alkylene chain having 2, 3, 4, 5, 6, 7, 8, 9 or 10 carbon atoms;

R(3) is R(10)—$C_nH_{2n}$—NR(11)— or R(10)—$C_nH_{2n}$—,
where one $CH_2$ group in the groups $C_nH_{2n}$ may be replaced by —O—, —CO—, —S—, —SO—, —$SO_2$— or —NR(12a)—; R(12a) is hydrogen, methyl or ethyl;
R(10) is hydrogen, methyl, cycloalkyl having 3, 4, 5, 6, 7 or 8 carbon atoms, $CF_3$, $C_2F_5$ or $C_3F_7$;
n is zero, 1, 2, 3, 4, 5, 6, 7, 8, 9 or 10;
R(11) is hydrogen or alkyl having 1, 2, 3, 4, 5 or 6 carbon atoms; or
R(10) and R(11)
together are a bond, if n is not less than 3; or R(3) together with R(4)
is an alkylene chain having 3, 4, 5, 6, 7 or 8 carbon atoms,
where a $CH_2$ group of the alkylene chain may be replaced by —O—, —CO—, —S—, —SO—, —$SO_2$— or —NR(12a)—; R(12a) is hydrogen, methyl or ethyl;

R(4) is R(13)—$C_rH_{2r}$,
where a $CH_2$ group of the group $C_rH_{2r}$ may be replaced by —O—, —CH=CH—, —C≡C—, —CO—, —CO—O—, —O—CO—, —S—, —SO—, —$SO_2$— or —NR(14)—;
R(14) is hydrogen or alkyl having 1, 2 or 3 carbon atoms;
R(13) is $CH_3$, $CF_3$, $C_2F_5$, $C_3F_7$, cycloalkyl having 3, 4, 5, 6, 7 or 8 carbon atoms, NR(15)R(16), phenyl or a nitrogen-containing heterocycle having 1, 2, 3, 4, 5, 6, 7, 8 or 9 carbon atoms,
where phenyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(15) and R(16)
together are a chain of 4 or 5 methylene groups of which one $CH_2$ group may be replaced by —O—, —S—, —NH—, —N(methyl)— or —N(benzyl)—;

r is zero, 1, 2, 3, 4, 5, 6, 7, 8, 9, 10, 11, 12, 13, 14, 15, 16, 17, 18, 19 or 20;

R(5) is —Y—$C_sH_{2s}$—R(18) or phenyl,
which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
Y is —O—, —S— or —NR(10c)—; R(10c) is hydrogen or alkyl having 1, 2 or 3 carbon atoms;
s is 1, 2, 3, 4, 5, 6, 7 or 8;
R(18) is hydrogen, $CF_3$, $C_2F_5$, $C_3F_7$, cycloalkyl having 3, 4, 5, 6, 7 or 8 carbon atoms, —COOR(21), NR(15a)R(16a), an unsubstituted nitrogen-containing heterocycle having 1, 2, 3, 4, 5, 6, 7, 8 or 9 carbon atoms, phenyl or thienyl,
where phenyl and thienyl are unsubstituted or substituted by 1 or 2 substituents selected from the group consisting of F, Cl, Br, I, $CF_3$, methyl, methoxy, sulfamoyl, methylsulfonyl and methylsulfonylamino;
R(15a) and R(16a)
together are a chain of 4 or 5 methylene groups of which one $CH_2$ group may be replaced by —O—, —S—, —NH—, —N(methyl)— or —N(benzyl)—;
R(21) is hydrogen or alkyl having 1, 2 or 3 carbon atoms;

R(6) is OR(10d) or OCOR(10d);
R(10d) is hydrogen or alkyl having 1, 2 or 3 carbon atoms;
B is hydrogen; or
R(6) and B
together are a bond; and their physiologically tolerable salts.

The present invention also relates to processes for preparing a compound of the formula I, to a pharmaceutical composition comprising an effective amount of said compound, together with a pharmaceutically acceptable carrier, and to the therapeutic treatment and/or prophylaxis of various syndromes with said compound or composition. Additional features and advantages of the invention are set forth in the description that follows, and, in part, will be apparent from the description or may be learned from practice of the invention. The advantages of the invention will be realized and attained by the compounds, processes, pharmaceutical compositions, therapeutic treatments and/or prophylaxes of various syndromes particularly pointed out in the written description and claims.

Both the foregoing general description and the following detailed description of the invention are exemplary and explanatory only and are not restrictive of the claimed invention.

Preference is given to compounds of the formula I in which R(1) and R(2)
independently of one another are hydrogen, $CF_3$, $C_2F_5$, $C_3F_7$ or alkyl having 1, 2, 3, 4, 5 or 6 carbon atoms; or
R(1) and R(2)
together are an alkylene chain having 2, 3, 4, 5, 6, 7, 8, 9 or 10 carbon atoms;
R(3) is R(10)—$C_nH_{2n}$;
R(10) is methyl, $CF_3$, $C_2F_5$ or $C_3F_7$;
n is zero, 1, 2, 3, 4, 5 or 6;
R(4) is R(13)—$C_rH_{2r}$,
where one $CH_2$ group of the group $C_rH_{2r}$ may be replaced by —O—, —CH=CH—, —C≡C—, —CO—, —CO—O—, —O—CO—, —S—, —SO—, —SO$_2$— or —NR(14)—;
R(14) is hydrogen or alkyl having 1, 2 or 3 carbon atoms;
R(13) is $CH_3$, $CF_3$, $C_2F_5$, $C_3F_7$, cycloalkyl having 3, 4, 5, 6, 7 or 8 carbon atoms, NR(15)R(16), phenyl or a nitrogen-containing heterocycle having 1, 2, 3, 4, 5, 6, 7, 8 or 9 carbon atoms,
where phenyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(15) and R(16)
together are a chain of 4 or 5 methylene groups of which one $CH_2$ group may be replaced by —O—, —S—, —NH—, —N(methyl)— or —N(benzyl)—;
r is zero, 1, 2, 3, 4, 5, 6, 7, 8, 9, 10, 11 or 12;
R(5) is —Y—$C_sH_{2s}$—R(18) or phenyl,
which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
Y is —O— or —S—;
s is 1, 2, 3, 4, 5, 6, 7 or 8;
R(18) is hydrogen, $CF_3$, $C_2F_5$, $C_3F_7$, cycloalkyl having 3, 4, 5, 6, 7 or 8 carbon atoms, —COOR(21), NR(15a)R(16a), an unsubstituted nitrogen-containing heterocycle having 1, 2, 3, 4, 5, 6, 7, 8 or 9 carbon atoms, phenyl or thienyl,
where phenyl and thienyl are unsubstituted or substituted by 1 or 2 substituents selected from the group consisting of F, Cl, Br, I, $CF_3$, methyl, methoxy, sulfamoyl, methylsulfonyl and methylsulfonylamino;
R(15a) and R(16a)
together are a chain of 4 or 5 methylene groups of which one $CH_2$ group may be replaced by —O—, —S—, —NH—, —N(methyl)— or —N(benzyl)—;
R(21) is alkyl having 1, 2 or 3 carbon atoms;
R(6) is OR(10d) or OCOR(10d);
R(10d) is hydrogen or alkyl having 1, 2 or 3 carbon atoms;
B is hydrogen; or
R(6) and B
together are a bond; and their physiologically tolerable salts.

Particular preference is given to compounds of the formula I in which R(5) is attached to the position labeled 6, i.e. to compounds of the formula Ia,

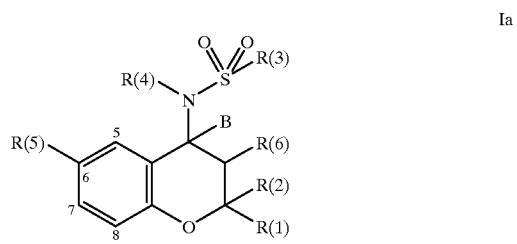

in which the radicals R(1), R(2), R(3), R(4), R(5), R(6) and B have the meanings given above as being preferred.

Very particular preference is given to compounds of the formula Ia in which R(1) and R(2)
independently of one another are hydrogen, $CF_3$ or alkyl having 1, 2 or 3 carbon atoms; or
R(1) and R(2)
together are an alkylene chain having 2, 3, 4, 5 or 6 carbon atoms;
R(3) is R(10)—$C_nH_{2n}$;
R(10) is methyl or $CF_3$;
n is zero, 1 or 2;
R(4) is R(13)—$C_rH_{2r}$,
where a $CH_2$ group of the group $C_rH_{2r}$ may be replaced by —O—, —CO—, —CO—O—, —O—CO—, —S—, —SO—, —SO$_2$— or —NR(14)—;
R(14) is hydrogen or alkyl having 1, 2 or 3 carbon atoms;
R(13) is $CH_3$, $CF_3$, NR(15)R(16), phenyl or a nitrogen-containing heterocycle having 1, 2, 3, 4, 5, 6, 7, 8 or 9 carbon atoms,
where phenyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(15) and R(16)
together are a chain of 4 or 5 methylene groups of which one $CH_2$ group may be replaced by —O—, —S—, —NH—, —N(methyl)— or —N(benzyl)—;
r is zero, 1, 2, 3, 4, 5, 6, 7 or 8;
R(5) is —Y—$C_sH_{2s}$—R(18);
Y is —O—;
s is 1, 2, 3, 4, 5 or 6;
R(18) is hydrogen, $CF_3$, —COOR(21), NR(15a)R(16a), an unsubstituted nitrogen-containing heterocycle having 1, 2, 3, 4, 5, 6, 7, 8 or 9 carbon atoms, phenyl or thienyl,
where phenyl and thienyl are unsubstituted or substituted by 1 or 2 substituents selected from the group consisting of F, Cl, Br, I, $CF_3$, methyl, methoxy, sulfamoyl, methylsulfonyl and methylsulfonylamino;
R(15a) and R(16a)
together are a chain of 4 or 5 methylene groups of which one $CH_2$ group may be replaced by —O—, —S—, —NH—, —N(methyl)— or —N(benzyl)—;

R(21) is alkyl having 1, 2 or 3 carbon atoms;
R(6) is OH;
B is hydrogen; or
R(6) and B
together are a bond;
and their physiologically tolerable salts.

Specific preference is given to compounds of the formula Ia in which R(1) and R(2)
are methyl;
R(3) is methyl or ethyl;
R(4) is R(13)—$C_rH_{2r}$,
where a $CH_2$ group of the group $C_rH_{2r}$ may be replaced by —O—, —CO—, —CO—O— or —O—CO;
R(13) is $CH_3$ or $CF_3$;
r is zero, 1, 2, 3, 4, 5, 6, 7 or 8;
R(5) is —Y—$C_sH_{2s}$—R(18);
Y is —O—;
s is 1, 2, 3, 4, 5 or 6;
R(18) is hydrogen, $CF_3$, —COOR(21), phenyl or thienyl,
where phenyl and thienyl are unsubstituted or substituted by 1 or 2 substituents selected from the group consisting of F, Cl, Br, $CF_3$, methyl or methoxy;
R(21) is alkyl having 1, 2 or 3 carbon atoms;
R(6) and B together are a bond;
and their physiologically tolerable salts.

Specific preference is also given to compounds of the formula Ia in which R(1) and R(2)
are methyl;
R(3) is methyl or ethyl;
R(4) is R(13)—$C_rH_{2r}$,
where a $CH_2$ group of the group $C_rH_{2r}$ may be replaced by —O—, —CO—, —CO—O— or —O—CO;
R(13) is $CH_3$ or $CF_3$;
r is zero, 1, 2, 3, 4, 5, 6, 7 or 8;
R(5) is —Y—$C_sH_{2s}$—R(18);
Y is —O—;
s is 1, 2, 3, 4, 5 or 6;
R(18) is hydrogen, $CF_3$, phenyl or thienyl,
where phenyl and thienyl are unsubstituted or substituted by 1 or 2 substituents selected from the group consisting of F, Cl, Br, $CF_3$, methyl or methoxy;
R(6) is OH;
B is hydrogen;
and their physiologically tolerable salts.

Alkyl radicals and alkylene radicals may be straight-chain or branched. This option also applies to the alkylene radicals of the formulae $C_rH_{2r}$, $C_nH_{2n}$ and $C_sH_{2s}$. Alkyl radicals and alkylene radicals may also be straight-chain or branched if they are substituted or a part of other radicals, for example in an alkoxy radical or in an alkylmercapto radical or in a fluorinated alkyl radical. Examples of alkyl radicals are methyl, ethyl, n-propyl, isopropyl, n-butyl, isobutyl, sec-butyl, tert-butyl, n-pentyl, isopentyl, neopentyl, n-hexyl, 3,3-dimethylbutyl, heptyl, octyl, nonyl, decyl, undecyl, dodecyl, tridecyl, tetradecyl, pentadecyl, hexadecyl, heptadecyl, octadecyl, nonadecyl, eicosyl. The divalent radicals derived from these radicals, for example methylene, 1,1-ethylene, 1,2-ethylene, 1,1-propylene, 1,2-propylene, 2,2-propylene, 1,3-propylene, 1,4-butylene, 1,5-pentylene, 2,2-dimethyl-1,3-propylene, 1,6-hexylene, etc., are examples of alkylene radicals.

Nitrogen-containing heterocycles having 1, 2, 3, 4, 5, 6, 7, 8 or 9 carbon atoms are in particular the aromatic systems 1-, 2- or 3-pyrrolyl, 1-, 2-, 4- or 5-imidazolyl, 1-, 3-, 4- or 5-pyrazolyl, 1,2,3-triazol-1-, -4- or 5-yl, 1,2,4-triazol-1-, -3- or -5-yl, 1- or 5-tetrazolyl, 2-, 4- or 5-oxazolyl, 3-, 4-5-isoxazolyl, 1,2,3-oxadiazol-4- or 5-yl, 1,2,4-oxadiazol-3- or 5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or 5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1- 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl.

Particular preference is given to the nitrogen-containing heterocycles pyrrolyl, imidazolyl, quinolyl, pyrazolyl, pyridyl, pyrazinyl, pyrimidinyl and pyridazinyl.

Thienyl is both 2- and 3-thienyl.

Mono-substituted phenyl radicals may be substituted in the 2-, the 3- or the 4-position, disubstituted phenyl radicals may be substituted in the 2,3-, 2,4-, 2,5-, 2,6-, 3,4- or 3,5-position. This substitution also applies correspondingly, in an analogous manner, to the nitrogen-containing heterocyles or to the thiophene radical.

If a radical is disubstituted, the substituents may be identical or different.

If the radicals R(1) and R(2) together are an alkylene chain, these radicals form, with the linking carbon atom, a ring which has a joint carbon atom with the 6-membered ring in the formula I, i.e. a spiro compound is present. If R(6) and B together are a bond, a 2H chromen skeleton is present. If R(10) and R(11) together are a bond, the group R(10)—$C_nH_{2n}$—NR(11)— is preferably a nitrogen heterocycle which is bonded via a nitrogen atom. If R(10) and R(11) together are a bond and the group R(10)—$C_nH_{2n}$—NR(11)— is a nitrogen heterocycle which is bonded via a nitrogen atom, this nitrogen heterocycle is preferably a 4-membered ring or a ring which is larger than a 4-membered ring, for example a 5-membered ring, 6-membered ring or 7-membered ring.

If the compounds of the formula I contain one or more acidic or basic groups or one or more basic heterocycles, the invention relates also to the corresponding physiologically or toxicologically tolerable salts, in particular to the pharmaceutically usable salts. Thus the compounds of the formula I which carry acidic groups, for example one or more COOH groups, can be used, for example, as alkali metal salts, preferably as sodium or potassium salts, or as alkaline earth metal salts, for example calcium or magnesium salts, or as ammonium salts, for example as salts with ammonia or organic amines or amino acids. Compounds of the formula I which carry one or more basic, i.e. protonatable groups or contain one or more basic heterocyclic rings, can also be used in the form of their physiologically tolerable acid addition salts with inorganic or organic acids, for example as hydrochlorides, phosphates, sulfates, methanesulfonates, acetates, lactates, maleates, fumarates, malates, gluconates etc. If the compounds of the formula I contain an acidic and basic group in the same molecule, beside the salt forms described, the invention also includes internal salts, so-called betaines. Salts can be obtained from the compounds of the formula I by customary processes, for example by combination with an acid or base in a solvent or dispersant, or else by anion exchange with other salts.

When appropriately substituted, the compounds of the formula I can be present in stereoisomeric forms. If the compounds of the formula I contain one or more centers of asymmetry, these can independently of one another have the S configuration or the R configuration. The invention includes all possible stereoisomers, e.g. enantiomers or diastereomers, and mixtures of two or more stereoisomeric forms, e.g. enantiomers and/or diastereomers, in any desired ratios. The invention thus relates to enantiomers, for example, in enantiomerically pure form, both as levo- and dextrorotatory antipodes, and also in the form of mixtures of the two enantiomers in different ratios or in the form of racemates. If cis/trans isomerism is present, the invention relates both to the cis form and to the trans form and mixtures of these forms. The preparation of individual stereoisomers can be carried out, if desired, by resolution of a mixture according to customary methods or, for example, by stereoselective synthesis. If mobile hydrogen atoms are present, the present invention also comprises all tautomeric forms of the compounds of the formula I.

The compounds of the formula I can be prepared by various chemical processes, which also form part of the subject matter of the present invention. Thus, for example, a compound of the formula I is obtained when a) a compound of the formula II

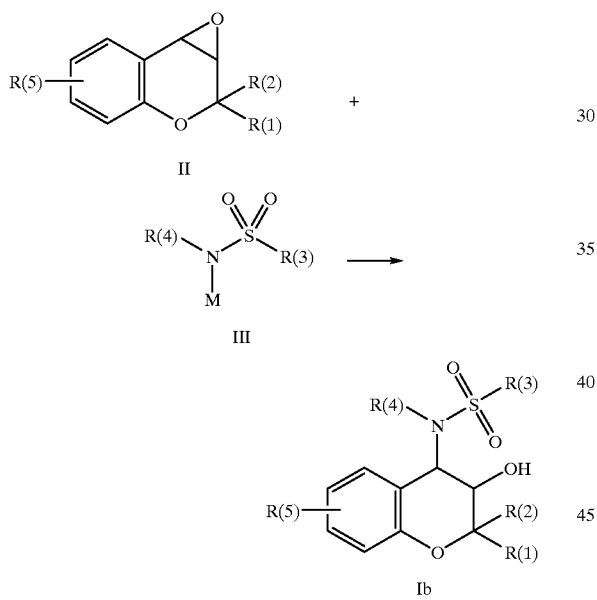

in which R(1), R(2) and R(5) are as defined above is reacted with a sulfonamide of the formula III in which R(3) and R(4) are as defined above and M is hydrogen or a metal equivalent, preferably lithium, sodium or potassium, or M is also advantageously a trialkylsilyl radical, for example a trimethylsilyl radical, to give a chromanol of the formula Ib; or when b) a compound of the formula Ib is reacted in a manner known per se with an alkylating agent of the formula R(10d)-L or an acylating agent of the formula R(10d)-COL or an anhydride of the formula (R(10d)-CO)$_2$O, in which R(10d) is as defined above and L is a nucleofugic leaving group, in particular F, Cl, Br, I, methanesulfonyloxy or p-toluenesulfonyloxy, in an alkylation or acylation reaction to give a compound of the formula Ic in which R(6) is OR(10d) or OCOR(10d);

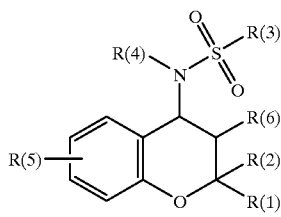

or when c) a compound of the formula Ib,

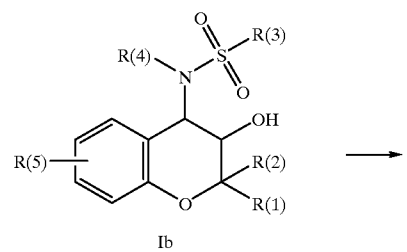

in which R(1), R(2), R(3), R(4) and R(5) are as defined above is converted in an elimination reaction to give a compound of the formula Id, in which R(1), R(2), R(3), R(4) and R(5) are as defined above;

or when d) a compound of the formula IV

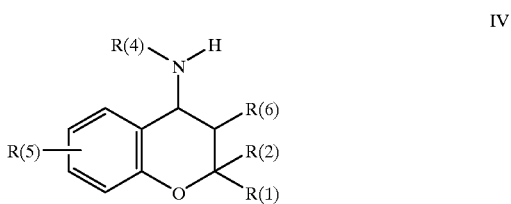

in which R(1), R(2), R(4), R(5) and R(6) are as defined in claims 1 to 6 is reacted with a sulfonic acid derivative of the formula V

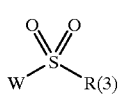

in which R(3) is as defined above and W is a nucleofugic leaving group, such as, for example, bromine, 1-imidazolyl, but in particular chlorine;

or when e) a compound of the formula VI

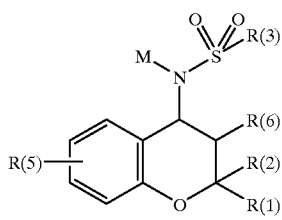

in which R(1), R(2), R(3), R(5) and R(6) are as defined in claims 1 to 6 and M is hydrogen or a metal equivalent, preferably lithium, sodium or potassium, in a manner known per se in an alkylation reaction with an alkylating agent of the formula VII

R(4)–L VII in which R(4) and L are as defined above; or when f) a compound of the formula VIII

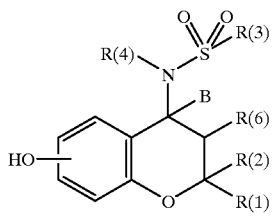

in which R(1), R(2), R(3), R(4), R(6) and B are as defined in claims 1 to 6 is reacted with a compound of the formula R(18)—C$_s$H$_{2s}$—L, in which R(18), s and L are as defined above in an alkylation reaction.

Procedure a)
corresponds to the nucleophilic opening of an epoxide of the formula II by a sulfonamide or a salt thereof of the formula III. If a free sulfonamide (formula III, M=H) is used, preference is given to initially generating a sulfonamide salt (formula III, M=metal cation) from this by action of a base, it being possible for the deprotonation of the sulfonamide to give the salt to be carried out in situ. For this purpose, preference is given to using bases which for their part do not react as a nucleophile, such as, for example, sodium hydride, sodium carbonate, potassium carbonate, sterically strongly hindered amines, for example dicyclohexylamine, N,N-dicyclohexylethylamine, or other strong nitrogen bases having low nucleophilicity, for example DBU (diazabicycloundecene), N,N',N'''-triisopropylguanidine, etc. However, it is also possible to employ other customarily used bases for the reaction, such as potassium tert-butoxide, sodium methoxide, alkali metal bicarbonates, alkali metal hydroxides, such as, for example, LiOH, NaOH or KOH, or alkaline earth metal hydroxides, such as, for example, Ca(OH)$_2$.

The base can be employed in a stoichiometric amount or else catalytically. The use of the free sulfonamide in the presence of a sub-stoichiometric amount, for example 20–70%, of a suitable base, for example sodium hydride, was found to be particularly advantageous.

The reaction is preferably carried out in a solvent, particularly preferably in polar organic solvents, such as, for example, dimethylformamide (DMF), dimethylacetamide (DMA), dimethyl sulfoxide (DMSO), tetramethylurea (TMU), hexamethylphosphoric triamide (HMPT), tetrahydrofuran (THF), dimethoxyethane (DME) or other ethers, or also, for example, in a hydrocarbon, such as toluene, or in a halogenated hydrocarbon, such as chloroform or methylene chloride and the like. However, the reaction can also be carried out in polar protic solvents, such as, for example, in water, methanol, ethanol, isopropanol, ethylene glycol or oligomers thereof and their corresponding semiethers or else their ethers. The reaction can also be carried out in mixtures of these solvents. However, the reaction can likewise be carried out very particularly preferably without solvent. The reaction is preferably carried out in a temperature range of from –10 to +140° C., particularly preferably in the range of from 20 to 100° C.

Another preferred procedure for carrying out this reaction entails the use of sulfonamide derivatives of the formula III where M is a trialkylsilyl, for example a trimethylsilyl, radical. Here, it is advantageous to carry out the reaction in the presence of a fluoride, for example tetrabutylammonium fluoride.

The epoxides of the formula II are obtained by methods known from the literature from the corresponding olefins of the formula IX,

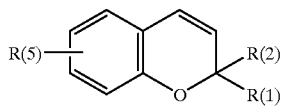

in which R(1), R(2) and R(5) are as defined in claims 1 to 6, for example by action of a suitable inorganic or organic peroxide, such as, for example, H$_2$O$_2$ or m-chloroperbenzoic acid, or by base-catalyzed cyclization of the corresponding bromohydrine, which can be obtained from IX, for example, by reaction with N-bromosuccinimide and water. The olefins of the formula IX can be obtained either from the ketones of the formula X by reduction of the carbonyl group to give an OH function and subsequent acid-catalyzed elimination, or by thermal cyclization of suitably substituted aryl propargyl ethers, such as described, for example, in J. Org. Chem. 38 (1973) 3832.

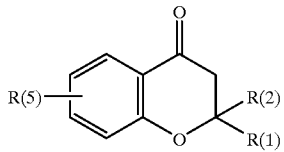

Procedure b)
describes the conversion of compounds of the formula Ib according to the invention into other compounds of the formula Ic according to the invention by alkylation or acylation of the 3-hydroxyl group. For the alkylation, the alcohol is additionally converted into an alkoxide salt by action of a suitable base, such as, for example, sodium hydride, and the alkoxide salt is then reacted with the alkylating agent of the formula R(10d)-L in a suitable polar solvent, such as, for example, dimethylformamide, at temperatures between 20 and 150° C. The deprotonation of the alcohol to give the salt can also be carried out in situ, in which case preference is given to using bases which for their part cannot be alkylated, such as, for example, potassium carbonate. Other suitable bases and solvents include those which have already been mentioned under procedure a). The acylation of the compounds of the formula Ib is preferably carried out by reaction with the corresponding anhydride of the formula $(R(10d)-CO)_2O$ in a suitable polar solvent, such as pyridine or dimethylformamide, and, if appropriate, with addition of an acylation catalyst, such as, for example, dimethylaminopyridine.

Procedure c)

describes the conversion of a chromanol of the formula Ib into a chromen of the formula Id by elimination. To this end, the chromanol can either be subjected directly to a dehydration in the presence of an acid or base, or the hydroxyl group can initially be activated, for example by acetylation with acetic anhydride (see procedure b) or mesylation with methanesulfonyl chloride, which may subsequently be followed by a base-catalyzed elimination, for example by heating with DBU (diazabicycloundecene).

Procedure d)

describes the frequently employed reaction, which is known per se, of a reactive sulfonyl compound of the formula V, in particular of a chlorosulfonyl compound (W=Cl), with an amino derivative of the formula IV to give the corresponding sulfonamide derivative of the formula I. In principle, the reaction can be carried out without solvent, but in most cases such reactions are carried out using a solvent. The reaction is preferably carried out using a polar solvent, preferably in the presence of a base which for its part may be used advantageously as solvent, for example when using triethylamine, in particular pyridine and its homologs. Solvents which are also used are, for example, water, aliphatic alcohols, for example methanol, ethanol, isopropanol, sec-butanol, ethylene glycol and its monomeric and oligomeric monoalkyl and dialkyl ethers, tetrahydrofuran, dioxane, dialkylated amides such as DMF, DMA, and also TMU and HMPT. The reaction is carried out at a temperature of from 0 to 160° C., preferably offrom 20 to 100° C.

The amines of the formula IV are obtained in a manner known from the literature preferably from the epoxides of the formula II by nucleophilic opening using the appropriate amines of the formula $R(4)-NH_2$, similar to the procedure described under a).

Procedure e)

represents the alkylation reaction, which is known per se, of a sulfonamide or one of its salts VI with an alkylating agent of the formula VII. To this end, the sulfonamide is initially converted into one of its salts, suitable bases and solvents for this purpose being those listed in procedure a), and the salt is then reacted with the alkylating agent of the formula VII at a temperature between 15 and 150° C.

The sulfonamides of the formula VI are obtained in a manner known from the literature preferably from the epoxides of the formula II by nucleophilic opening using the appropriate sulfonamides of the formula $R(3)-SO_2NH_2$, similar to the procedure described under a), it being advantageous here, however, to employ a stoichiometric amount of base.

Procedure f)

describes the alkylation of a phenol of the formula VIII with an alkylating agent of the formula $R(18)-C_sH_{2s}-L$. To this end, the phenol is initially converted, by action of a suitable base, such as, for example, sodium hydride or a phosphazene base, into a phenolate salt, which is then reacted with the alkylating agent in a suitable polar solvent, such as, for example, dimethylformamide or dimethylacetamide, at temperatures between 20 and 150° C. The deprotonation of the alcohol to give the salt can also be carried out in situ, it being preferred in this case to employ bases which for their part are not alkylated, such as, for example, potassium carbonate. Other suitable bases and solvents which can be used include those which have already been mentioned under procedure a).

The phenols of the formula VIII are obtained using the methods described under a) to e), but R(5) is then in each case OH or OR (R=suitable protective group, for example benzyl), and in the latter case a subsequent removal of the protective group is carried out.

In all procedures, it may be appropriate to protect functional groups in the molecule temporarily in certain reaction steps. Such protective group techniques are familiar to the person skilled in the art. The choice of a protective group for groups in question and the methods for their introduction and removal are described in the literature and can be adapted to the individual case, where appropriate, without difficulties.

It has already been said that the compounds of the formula I surprisingly have a strong and specific blocking (closing) action on a $K^+$ channel which is opened by cyclic adenosine monophosphate (cAMP) and fundamentally differs from the well-known $K^+$ (ATP) channel, and that this $K^+$ (cAMP) channel identified in colonic tissue is very similar, perhaps even identical, to the $I_{Ks}$ channel identified in the cardiac muscle. For the compounds according to the invention, it was possible to show a strong blocking action on the $I_{Ks}$ channel in guinea-pig cardiomyocytes and on the $I_{sK}$ channel expressed in Xenopus oocytes. As a result of this blocking of the $K^+$ (cAMP) channel or of the $I_{Ks}$ channel, the compounds according to the invention display pharmacological actions of high therapeutic utility in the living body and are outstandingly suitable as pharmaceutical active compounds for the therapy and prophylaxis of various syndromes.

The compounds of the formula I according to the invention are thus distinguished as a novel active compound class of potent inhibitors of stimulated gastric acid secretion. The compounds of the formula I are thus useful pharmaceutical active compounds for the therapy and prophylaxis of ulcers of the stomach and of the intestinal region, for example of the duodenum. They are likewise suitable, on account of their strong gastric juice secretion-inhibiting action, as excellent therapeutics for the therapy and prophylaxis of reflux esophagitis.

The compounds of the formula I according to the invention are furthermore distinguished by an antidiarrheal action and are therefore suitable as pharmaceutical active compounds for the therapy and prophylaxis of diarrheal illnesses.

The compounds of the formula I according to the invention are furthermore suitable as pharmaceutical active compounds for the therapy and prophylaxis of cardiovascular disorders. In particular, they can be used for the therapy and prophylaxis of all types of arrhythmias, including atrial, ventricular and supraventricular arrhythmias, especially cardiac arrhythmias which can be eliminated by action potential prolongation. They can be specifically used for the therapy and prophylaxis of atrial fibrillation and atrial flutters, and for the therapy and prophylaxis of reentry arrhythmias and for the prevention of sudden heart death as a result of ventricular fibrillation.

Athough numerous substances having antiarrhythmic activity are already on the market, there is nevertheless no compound which is really satisfactory with respect to activity, range of application and side-effect profile, so that there is furthermore a need for the development of improved antiarrhythmics. The action of numerous known antiarrhythmics of the so-called class IIII is based on an increase in the myocardial refractory time by prolongation of the action potential duration. This is essentially determined by the extent of repolarizing K$^+$ streams which flow out of the cell via various K$^+$ channels. Particularly great importance is ascribed in this context to the so-called "delayed rectifier" I$_K$, of which two subtypes exist, a rapidly activated I$_{Kr}$ and a slowly activated I$_{Ks}$. Most known class III antiarrhythmics block I$_{Kr}$ predominantly or exclusively (e.g. dofetilide, d-sotalol). It has been shown, however, that these compounds have an increased proarrhythmic risk at low or normal heart rates, arrhythmias which are designated as "Torsades de pointes" in particular being observed (D. M. Roden; "Current Status of Class III Antiarrhythmic Drug Therapy"; Am. J. Cardiol. 72 (1993), 44B–49B). In the case of higher heart rates or stimulation of the β-receptors, however, the action potential-prolonging action of the I$_{Kr}$ blockers is markedly reduced, which is attributed to the fact that under these conditions the I$_{Ks}$ contributes more strongly to the repolarization. For these reasons, the substances according to the invention, which act as I$_{Ks}$ blockers, have significant advantages compared with the known I$_{Kr}$ blockers. In the meantime, it has also been described that a correlation exists between I$_{Ks}$ channel-inhibitory action and the suppression of life-threatening cardiac arrhythmias, such as are elicited, for example, by β-adrenergic hyperstimulation (e.g. T. J. Colatsky, C. H. Follmer and C. F. Starmer; "Channel Specificity in Antiarrhythmic Drug Action; Mechanism of potassium channel block and its role in suppressing and aggravating cardiac arrhythmias"; Circulation 82 (1990), 2235–2242; A. E. Busch, K. Malloy, W. J. Groh, M. D. Varnum, J. P. Adelman and J. Maylie; "The novel class III antiarrhythmics NE-10064 and NE-10133 inhibit I$_{sK}$ channels in Xenopus oocytes and I$_{Ks}$ in guinea pig cardiac myocytes"; Biochem. Biophys. Res. Commun. 202 (1994), 265–270).

Moreover, the compounds contribute to a marked improvement of cardiac insufficiency, in particular of congestive heart failure, advantageously in combination with contraction-promoting (positively inotropic) active compounds, e.g. phosphodiesterase inhibitors.

In spite of the therapeutically utilizable advantages which can be achieved by a blockade of the I$_{Ks}$, hitherto only very few compounds have been described which inhibit this subtype of the "delayed rectifier." The substance azimilide which is in development admittedly also has a blocking action on the I$_{Ks}$, but mainly blocks the I$_{Kr}$ (selectivity 1:10). WO-A-95/14470 claims the use of benzodiazepines as selective blockers of the I$_{Ks}$. Further I$_{Ks}$ blockers are described in FEBS Letters 396 (1996), 271–275: "Specific blockade of slowly activating I$_{sK}$ channels by chromanols . . . " and Pflügers Arch.—Eur. J. Physiol. 429 (1995), 517–530: "A new class of inhibitors of cAMP-mediated Cl-secretion in rabbit colon, acting by the reduction of cAMP-activated K$^+$ conductance". The potency of the 3-hydroxychromanols described there, however, is lower than that of the compounds of the formula I according to the invention.

The compounds of the formula I according to the invention and their physiologically tolerable salts can thus be used in animals, preferably in mammals, and in particular in humans as pharmaceuticals per se, in mixtures with one another or in the form of pharmaceutical preparations. The present invention also relates to the compounds of the formula I and their physiologically tolerable salts for use as pharmaceuticals, their use in the therapy and prophylaxis of the syndromes mentioned and their use for the production of medicaments therefor and of medicaments with K$^+$ channel-blocking action. Furthermore, the present invention relates to pharmaceutical preparations which, as active constituent, contain an effective dose of at least one compound of the formula I and/or of a physiologically tolerable salt thereof in addition to customary, pharmaceutically innocuous excipients and auxiliaries. The pharmaceutical preparations normally contain 0.1 to 90 percent by weight of the compounds of the formula I and/or of their physiologically tolerable salts. The pharmaceutical preparations can be prepared in a manner known per se. For this purpose, the compounds of the formula I and/or their physiologically tolerable salts, together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain compounds of the formula I according to the invention and/or their physiologically tolerable salts can be administered orally, parenterally, e.g. intravenously, rectally, by inhalation or topically, the preferred administration being dependent on the individual case, e.g. the particular course of the illness to be treated.

The person skilled in the art is familiar, on the basis of his expert knowledge, with the auxiliaries which are suitable for the desired pharmaceutical formulation. Beside solvents, gel-forming agents, suppository bases, tablet auxiliaries and other active compound carriers, it is possible to use, for example, antioxidants, dispersants, emulsifiers, antifoams, flavor corrigents, preservatives, solubilizers, agents for achieving a depot effect, buffer substances or colorants.

The compounds of the formula I can also be combined with other pharmaceutical active compounds to achieve an advantageous therapeutic effect. Thus in the treatment of cardiovascular disorders, advantageous combinations with substances having cardiovascular activity are possible. Possible combination components of this type which are advantageous for cardiovascular disorders are, for example, other antiarrhythmics, i.e. class I, class II or class III antiarrhythmics, such as, for example I$_{Kr}$ channel blockers, e.g. dofetilide, or furthermore hypotensive substances such as ACE inhibitors (for example enalapril, captopril, ramipril), angiotensin antagonists, K$^+$ channel activators and also alpha- and beta-receptor blockers, but also sympathomimetic compounds and compounds having adrenergic activity, and also Na$^+$/H$^+$ exchange inhibitors, calcium channel antagonists, phosphodiesterase inhibitors and other substances having positively inotropic activity, such as, for example, digitalis glycosides, or diuretics. Combinations with substances having antibiotic activity and with antiulcer agents are furthermore advantageous, for example with H$_2$ antagonists (e.g. ranitidine, cimetidine, famotidine, etc.), in particular when used for the treatment of gastrointestinal disorders.

For an oral administration form, the active compounds are mixed with the additives suitable for this purpose, such as excipients, stabilizers or inert diluents, and brought by the customary methods into the suitable administration forms, such as tablets, coated tablets, hard capsules, aqueous, alcoholic or oily solutions. Inert excipients which can be used are, for example, gum arabic, magnesia, magnesium carbonate, potassium phosphate, lactose, glucose or starch, in particular corn starch. In this case the preparation can be carried out either as dry or as moist granules. Suitable oily excipients or solvents are, for example, vegetable or animal oils, such as sunflower oil or cod-liver oil. Suitable solvents for aqueous or alcoholic solutions are, for example, water, ethanol or sugar solutions or mixtures thereof. Further auxiliaries, also for other administration forms, are, for example, polyethylene glycols and polypropylene glycols.

For subcutaneous or intravenous administration, the active compounds, if desired with the substances customary for this such as solubilizers, emulsifiers or further auxiliaries, are brought into solution, suspension or emulsion. The compounds of the formula I and their physiologically tolerable salts can also be lyophilized and the lyophilisates obtained can be used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulation for administration in the form of aerosols or sprays are, for example, solutions, suspensions or emulsions of the active compounds of the formula I or their physiologically tolerable salts in a pharmaceutically acceptable solvent, such as, in particular, ethanol or water, or a mixture of such solvents. If required, the formulation can also additionally contain other pharmaceutical auxiliaries such as surfactants, emulsifiers and stabilizers as well as a propellant. Such a preparation contains the active compound customarily in a concentration from approximately 0.1 to 10, in particular from approximately 0.3 to 3, percent by weight.

The dose of the active compound of the formula I or of the physiologically tolerable salts thereof to be administered depends on the individual case and, as customary, is to be adapted for an optimum effect to the conditions of the individual case. Thus it depends, of course, on the frequency of administration and on the potency and duration of action of the compounds employed in each case for therapy or prophylaxis, but also on the nature and severity of the disease to be treated and on the sex, age, weight and individual responsiveness of the human or animal to be treated and on whether the therapy is acute or prophylactic. Customarily, the daily dose of a compound of the formula I in the case of administration to a patient approximately 75 kg in weight is 0.001 mg/kg of body weight to 100 mg/kg of body weight, preferably 0.01 mg/kg of body weight to 20 mg/kg of body weight. The dose can be administered in the form of an individual dose or divided into several, e.g. two, three or four, individual doses. In particular in the treatment of acute cases of cardiac arrhythmias, for example in an intensive care unit, parenteral administration by injection or infusion, e.g. by an intravenous continuous infusion, can also be advantageous.

It is also possible to employ the compounds of the formula I, as already mentioned above, as intermediates for preparing other pharmaceutically active compounds.

The present invention is further illustrated by the following examples which are designed to teach those of ordinary skill in the art how to practice the invention. The following examples are merely illustrative of the invention and should not be construed as limiting the invention as claimed.

Experimental part
List of abbreviations

| | |
|---|---|
| DBU | 1,8-diazabicyclo[5.4.0]undec-7-ene |
| DMF | N,N-dimethylformamide |
| DMSO | dimethyl sulfoxide |
| EA | ethyl acetate |
| m.p. | melting point (unless stated otherwise, the melting points of |

-continued

| | |
|---|---|
| | the unpurified crude products are given; it is well possible that the melting points of the respective pure substances are considerably higher) |
| i. vac. | in vacuo |
| sol. | solvent |
| NBS | N-bromosuccinimide |
| RT | room temperature |
| THF | tetrahydrofuran |

EXAMPLE 1

(±)-trans-N-(6-Benzyloxy-3-hydroxy-2,2-dimethylchroman-4-yl)-N-methylmethanesulfonamide

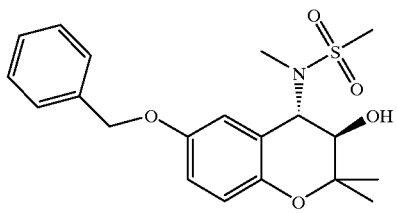

a) 2,2-Dimethyl-6-hydroxychroman-4-one

A reaction mixture of 100 g (0.65 mol) of 2,5-dihydroxyacetophenone in 1 l of acetonitrile, 130 ml (1.55 mol) of pyrrolidine and 290 ml (3.95 mol) of acetone was heated at 45° C. for 8 h. The sol. were then removed i. vac. and the residue was dissolved in 1 l of EA. The organic phase was washed twice with dilute hydrochloric acid, stirred with activated carbon and dried over magnesium sulfate and substantially concentrated. The residue was stirred with petroleum ether and the precipitate was filtered off with suction giving 102 g of 2,2-dimethyl-6-hydroxychroman-4-one, m.p. 161° C.

b) 6-Benzyloxy-2,2-dimethylchroman-4-one

At RT, 25.2 g (131.2 mmol) of 6-hydroxy-2,2-dimethylchroman-4-one were introduced with stirring into 350 ml of diethyl ketone and, after addition of 18.0 g (131 mmol) of powdered potassium carbonate, stirred at 75° C. for 30 min. After cooling to 60° C., 15.7 ml (131 mmol) of benzyl bromide were added dropwise, and after 2 h the mixture was concentrated i. vac., the residue was treated with water and the solid was filtered off with suction, 37 g, m.p. 109–110° C.

c) 6-Benzyloxy-2,2-dimethylchroman-4-ol

A solution of 20.0 g (71 mmol) of 6-benzyloxy-2,2-dimethylchroman-4-one and 2.94 g (78 mmol) of sodium borohydride in 100 ml of methanol and 300 ml of ethanol was stirred at RT for 3 h. The reaction mixture was then poured into 1300 ml of ice-water, and the precipitate was filtered off with suction and dried under reduced pressure. This procedure gave 19.3 g of 6-benzyloxy-2,2-dimethylchroman-4-ol, m.p. 83–84° C.

d) 6-Benzyloxy-2,2-dimethyl-2H-chromen

A solution of 9.6 g (33.8 mmol) of 6-benzyloxy-2,2-dimethylchroman-4-ol and 0.2 g of p-toluenesulfonic acid in 85 ml of toluene was heated under reflux on a water separator for 1 h. After cooling, the mixture was washed twice with sodium bicarbonate solution, dried over magnesium sulfate and concentrated i. vac., giving 7.6 g of 6-benzyloxy-2,2-dimethyl-2H-chromen.

e) 6-Benzyloxy-3-bromo-2,2-dimethylchroman-4-ol

With efficient stirring, 5.05 g (28.3 mmol) of NBS were added all at once to a solution of 7.5 g (28. 2 mmol) of 6-benzyloxy-2,2-dimethyl-2H-chromen in 108 ml of DMSO and 0.9 ml (48.7 mmol) of water, and the mixture was stirred at RT overnight. The reaction mixture was poured into 450 ml of water and stirred for another hour and the precipitate was filtered off with suction, washed with water and dried under reduced pressure. This gave 9.5 g of 6-benzyloxy-3-bromo-2,2-dimethylchroman-4-ol, m.p. 126–128° C.

f) 6-Benzyloxy-2,2-dimethyl-3,4-epoxychroman

A solution of 9.5 g (28.5 mmol) of 6-benzyloxy-3-bromo-2,2-dimethyl-chroman-4-ol in 100 ml of THF was stirred overnight with 4.6 g (82 mmol) of potassium hydroxide powder. The batch was subsequently filtered through Celite and the filtrate was concentrated using a rotary evaporator, giving 8.3 g of 6-benzyloxy-2,2-dimethyl-3,4-epoxychroman, m.p. 70–72° C.

g) N-(6-Benzyloxy-3-hydroxy-2,2-dimethylchroman-4-yl)-N-methyl-methanesulfonamide 4.25 g (39 mmol) of methyl-methanesulfonamide in 7.5 ml of DMSO were added dropwise to a suspension of 0.21 g (7 mmol) of 80 percent sodium hydride in 15 ml of DMSO, and the mixture was stirred at RT for 30 min. 8.2 g (29 mmol) of 6-benzyloxy-2,2-dimethyl-3,4-epoxychroman, dissolved in 18 ml of DMSO were then added dropwise, and the batch was heated at 50° C. for 2 days. The mixture was subsequently poured into water and the precipitate was filtered off with suction and dried well under reduced pressure, giving 8.8 g of N-(6-benzyloxy-3-hydroxy-2,2-dimethylchroman-4-yl)-N-methyl-methanesulfonamide, m.p. 162–164° C.

EXAMPLE 2

(±)-trans-N-(6-Benzyloxy-3-acetoxy-2,2-dimethylchroman-4-yl)-N-methyl-methanesulfonamide

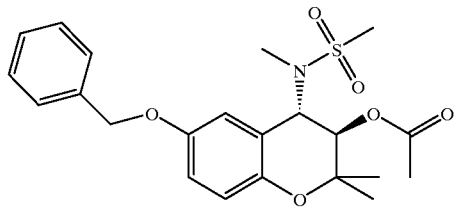

A solution of 4.5 g of N-(6-benzyloxy-3-hydroxy-2,2-dimethylchroman-4-yl)-N-methyl-methanesulfonamide and 37 ml of acetic anhydride in 74 ml of pyridine was left to stand at RT overnight. The batch was concentrated under reduced pressure and the residue was dissolved in EA, washed successively with dilute hydrochloric acid and saturated sodium bicarbonate solution and dried over magnesium sulfate. Removal of the solvent under reduced pressure gave 4.7 g of N-(6-benzyloxy-3-acetoxy-2,2-dimethylchroman-4-yl)-N-methyl-methanesulfonamide, m.p. 124–125° C.

EXAMPLE 3

(±)-trans-N-(6-Benzyloxy-3-methoxy-2,2-dimethylchroman-4-yl)-N-methyl-methanesulfonamide

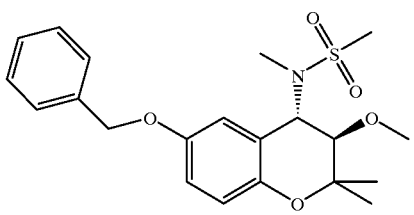

0.5 g (1.3 mmol) of N-(6-benzyloxy-3-hydroxy-2,2-dimethylchroman-4-yl)-N-methyl-methanesulfonamide (Example 1g) dissolved in 4 ml of DMF was added dropwise to a suspension of 0.05 g (1.7 mmol) of sodium hydride in 3 ml of DMF. The mixture was stirred at RT for 30 min, 0.25 g (1.8 mmol) of methyl iodide was added, and the mixture was stirred at RT for another 3 h. The reaction mixture was concentrated under reduced pressure, the residue was taken up in water and EA and the organic phase was washed with dilute hydrochloric acid and saturated sodium bicarbonate solution. Drying over magnesium sulfate and concentration under reduced pressure gave 0.52 g of N-(6-benzyloxy-3-methoxy-2,2-dimethylchroman-4-yl)-N-methyl-methanesulfonamide, m.p. 119–121° C.

EXAMPLE 4

N-(6-Benzyloxy-2,2-dimethyl-2H-chromen-4-yl)-N-methyl-methanesulfonamide

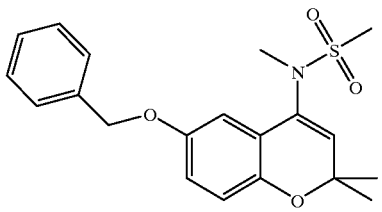

A solution of 1.0 g (2.3 mmol) of N-(6-benzyloxy-3-acetoxy-2,2-dimethylchroman-4-yl)-N-methyl-methanesulfonamide (Example 2) and 2.1 g (13.8 mmol) of DBU in 4.2 ml of toluene was heated at 105° C. for 5 h. The reaction mixture was diluted with EA and washed with hydrochloric acid until the aqueous phase gave an acidic reaction. The mixture was washed with sodium bicarbonate solution, dried over magnesium sulfate and concentrated i. vac., giving 0.85 g of N-(6-benzyloxy-2,2-dimethyl-2H-chromen-4-yl)-N-methyl-methanesulfonamide.

EXAMPLE 5

(±)-trans-N-(6-Butoxy-3-hydroxy-2,2-dimethylchroman-4-yl)-N-methyl-methanesulfonamide

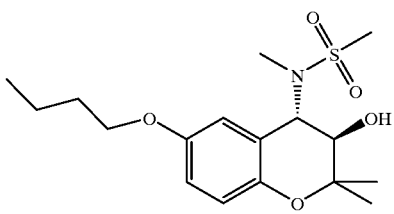

a) 6-Butoxy-2,2-dimethylchroman-4-one

A solution of 50 g (0.26 mol) of 2,2-dimethyl-6-hydroxychroman-4-one (Example 1a) in 500 ml of DMF was added dropwise to a suspension of 9.0 g (0.3 mol) of 80 percent sodium hydride in 500 ml of DMF. The mixture was stirred at RT for 90 min, 49 g (0.265 mol) of iodobutane were added and the mixture was stirred at RT for a further 90 min. The reaction mixture was then concentrated under reduced pressure and the residue was admixed with water and extracted repeatedly with EA. The organic phases were washed with 5 M aqueous sodium hydroxide solution, stirred with activated carbon and magnesium sulfate, filtered and concentrated. This procedure gave 57.6 g of 6-butoxy-2,2-dimethylchroman-4-one.

b) 6-Butoxy-2,2-dimethyl-2H-chromen was obtained from 6-butoxy-2,2-dimethylchroman-4-one similarly to the procedure described in Examples 1c and 1d. Alternatively, the compound was also obtained by the following route: Initially, 4.5 g (150 mmol) of 80 percent sodium hydride and, after 15 min, a solution of 23 g (224 mmol) of 3-chloro-3-methylbutyne was added dropwise at RT to a solution of 25 g of 4-butoxyphenol (150 mmol) in 350 ml toluene, and the mixture was then heated under reflux for 10 h. After cooling, the mixture was washed with 5 M of aqueous sodium hydroxide solution and water and concentrated under reduced pressure, and the residue was purified by silica gel chromatography usiny cyclohexane/EA 9:1.

c) 6-Butoxy-3-bromo-2,2-dimethylchroman-4-ol was obtained from 6-butoxy-2,2-dimethyl-2H-chromen similarly to the procedure described in Example 1e; m.p. 72–74° C.

d) 6-Butoxy-2,2-dimethyl-3,4-epoxychroman

Similar to Example 1f, 1.0 g (3 mmol) of 6-butoxy-3-bromo-2,2-dimethylchroman-4-ol gave 0.8 g of 6-butoxy-2, 2-dimethyl-3,4-epoxychroman as an oil.

e) N-(6-Butoxy-3-hydroxy-2,2-dimethyl-chroman-4-yl)-N-methyl-methanesulfonamide 0.47 g (4.3 mmol) of N-methyl-methanesulfonamide in 1 ml of DMSO were added dropwise to a suspension of 0.02 g (0.7 mmol) of 80 percent sodium hydride in 2 ml of DMSO, and the mixture was stirred at RT for 30 min. 0.8 g (3.2 mmol) of 6-butoxy-2,2-dimethyl-3,4-epoxychroman, dissolved in 1 ml of DMSO, was then added dropwise, and the batch was left to stand at RT for 5 days and then heated at 50° C. for a further 9 h. The mixture was subsequently poured into water and the precipitate was filtered off with suction and dried thoroughly under reduced pressure, giving 0.82 g of N-(6-butoxy-3-hydroxy-2,2-dimethyl-chroman-4-yl)-N-methyl-methanesulfonamide, m.p. 138–140° C.

EXAMPLE 6

(±)-trans-N-(3-Acetoxy-6-butoxy-2,2-dimethylchroman-4-yl)-N-methyl-methanesulfonamide

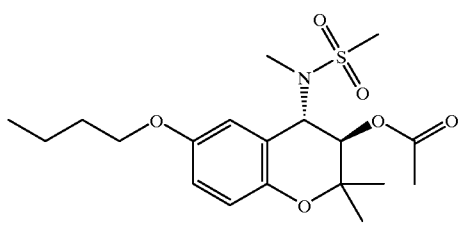

Similar to Example 2, 0.7 g of N-(6-butoxy-3-hydroxy-2,2-dimethylchroman-4-yl)-N-methyl-methanesulfonamide and 6.5 ml of acetic anhydride in 13 ml of pyridine gave 0.6 g of N-(3-acetoxy-6-butoxy-2,2-dimethylchroman-4-yl)-N-methyl-methanesulfonamide; m.p. 87–89° C.

EXAMPLE 7

N-(6-Butoxy-2,2-dimethyl-2H-chromen-4-yl)-N-methyl-methanesulfonamide

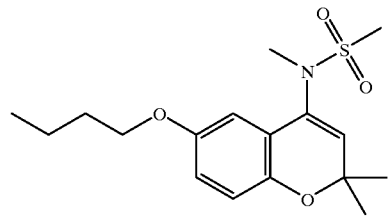

A solution of 0.5 g (1.3 mmol) of N-(6-butoxy-3-acetoxy-2,2-dimethylchroman-4-yl)-N-methyl-methanesulfonamide (Example 6) and 1.1 g (7.5 mmol) of DBU in 2.5 ml of toluene was heated at 105° C. for 60 h. The reaction mixture was diluted with EA and washed with hydrochloric acid until the aqueous phase gave an acidic reaction. The mixture was washed with sodium bicarbonate solution, dried over magnesium sulfate and concentrated i. vac., giving 0.3 9 of N-(6-butoxy-2,2-dimethyl-2H-chromen-4-yl)-N-methyl-methanesulfonamide; m.p. 114–116° C.

EXAMPLE 8

(±)-trans-N-(6-Propoxy-3-hydroxy-2,2-dimethylchroman-4-yl)-N-methyl-methanesulfonamide

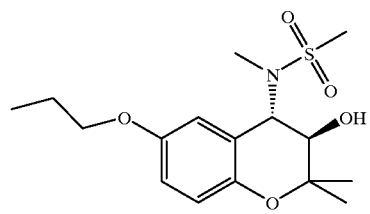

a) N-(3,6-Dihydroxy-2,2-dimethylchroman-4-yl)-N-methyl-methanesulfonamide 1.0 g (2.6 mmol) of (±)-trans-N-(6-benzyloxy-3-hydroxy-2,2-dimethylchroman-4-yl)-N-methyl-methanesulfonamide (Example 1) was hydrogenated in 100 ml of THF/methanol (1:1) in the presence of palladium/carbon until the uptake of hydrogen had ended. The catalyst was filtered off and the filtrate was concentrated, giving 0.7 g of N-(3,6-dihydroxy-2,2-dimethylchroman-4-yl)-N-methyl-methanesulfonamide; m.p. 204–206° C.

b) 0.45 g (1.5 mmol) of the above compound, dissolved in 5 ml of DMF, was added dropwise to a solution of 50 mg (1.6 mmol) of 80 percent sodium hydride in 2 ml of DMF. After 2 h at RT, 0.27 g (1.6 mmol) of 1-iodopropane were added and the mixture was stirred at RT for 2 days. Work-up and recrystallization from isopropanol gave 0.22 g of (±)-trans-N-(6-propoxy-3-hydroxy-2,2-dimethylchroman-4-yl)-N-methyl-methanesulfonamide; m.p. 149–151° C.

EXAMPLE 9
N-(6-Propoxy-2,2-dimethyl-2H-chromen-4-yl)-N-methyl-methanesulfonamide

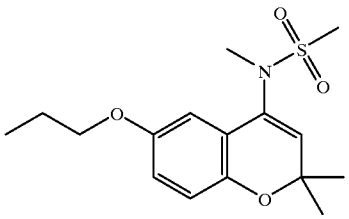

a) Hydrogenation of 3.3 g of (±)-trans-N-(6-benzyloxy-3-acetoxy-2,2-dimethylchroman-4-yl)-N-methyl-methanesulfonamide (Example 2) in the presence of Pd/C gave 2.6 g of (±)-trans-N-(6-hydroxy-3-acetoxy- 2,2-dimethylchroman-4-yl)-N-methyl-methanesulfonamide; m.p. 172–174° C.

b) Subsequent reaction with DBU in toluene similar to Example 7 gave, after silica gel chromatography and recrystallization from toluene/EA, 1.2 g of N-(6-hydroxy-2,2-dimethyl-2H-chromen-4-yl)-N-methyl-methanesulfonamide; m.p. 130–132° C.

c) Similar to Example 8b, 0.5 g of N-(6-hydroxy-2,2-dimethyl-2H-chromen-4-yl)-N-methyl-methanesulfonamide was alkylated with 1-iodopropane, giving 0.36 g of N-(6-propoxy-2,2-dimethyl-2H-chromen-4-yl)-N-methyl-methanesulfonamide; m.p. 93–95° C.

EXAMPLE 10
(±)-trans-N-(6-Benzyloxy-3-hydroxy-2,2-dimethylchroman-4-yl)-N-butyl-methanesulfonamide

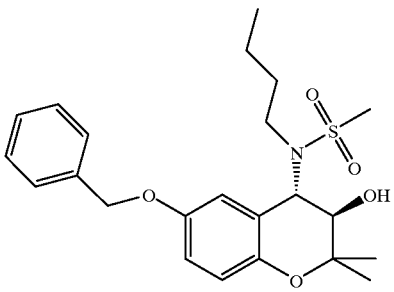

a) (±)-trans-N-(6-Benzyloxy-3-hydroxy-2,2-dimethylchroman-4-yl)-methanesulfonamide A reaction mixture of 0.47 g (16 mmol) of 80 percent sodium hydride, 1.75 g (18 mmol) of methanesulfonamide and 4.0 g (14 mmol) of 6-benzyloxy-2,2-dimethyl-3,4-epoxychroman (Example 1f) in 25 ml of DMSO was heated at 50° C. for 36 h. The reaction mixture was then poured into ice-water and the precipitated product was filtered off with suction and recrystallized from isopropanol/petroleum ether. This procedure gave 2.9 g of the title compound having a melting point of 181–182° C.

b) A solution of 1.0 g (2.6 mmol) of the above compound and 90 mg (2.9 mmol) of 80 percent sodium hydride in 13 ml of DMF was stirred at RT for 1 h. 0.51 g (2.8 mmol) of 1-iodobutane was then added, and the batch was heated at 50° C. for 10 h. The reaction mixture was concentrated under reduced pressure and the residue was taken up in EA and washed with water. Purification by silica gel chromatography using cyclohexane/EA 3:1 gave 0.5 g of (±)-trans-N-(6-benzyloxy-3-hydroxy-2,2-dimethylchroman- 4-yl)-N-butyl-methanesulfonamide; m.p. 159–160° C.

EXAMPLE 11
N-(6-Benzyloxy-2,2-dimethyl-2H-chromen-4-yl)-N-methyl-methanesulfonamide

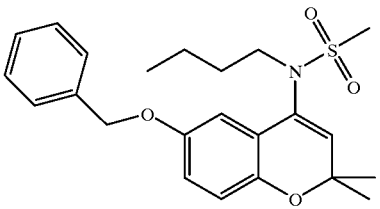

The compound was obtained from (±)-trans-N-(6-benzyloxy-3-hydroxy-2,2-dimethylchroman-4-yl)-N-butyl-methanesulfonamide (Example 10), similarly to the method described in Examples 2 and 4. m.p. 74–76° C.

EXAMPLE 12
Methyl (±)-trans-[(6-benzyloxy-3-hydroxy-2,2-dimethylchroman-4-yl)-methanesulfonylamino]acetate

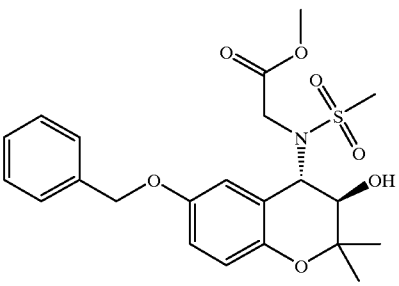

0.9 g of (±)-trans-N-(6-benzyloxy-3-hydroxy-2,2-dimethylchroman-4-yl)-methanesulfonamide (Example 10a) gave, by alkylation with methyl bromoacetate similar to Example 10b, 0.5 g of methyl (±)-trans-[(6-benzyloxy-3-hydroxy-2,2-dimethylchroman-4-yl)-methanesulfonylamino]-acetate; m.p. 133–135° C.

EXAMPLE 13
(±)-trans-N-[3-Hydroxy-2,2-dimethyl-6-(4,4,4-trifluorobutoxy)-chroman-4-yl]-N-methyl-methanesulfonamide

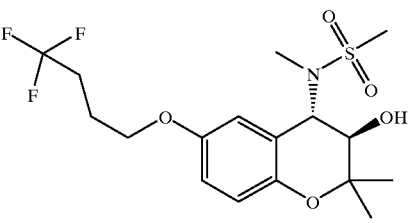

a) (±)-trans-N-[3,6-Dihydroxy-2,2-dimethyl)chroman-4-yl]-N-methyl-methanesulfonamide 2.0 g (5 mmol) of (±)-trans-N-(6-benzyloxy-3-hydroxy-2,2-dimethylchroman-4-yl)-N-methyl-methanesulfonamide (Example 1) were hydrogenated at atmospheric pressure in 200 ml of THF/methanol (1:1) in the presence of palladium/activated carbon (5% Pd) until the hydrogen uptake had ended. The catalyst was filtered off and the mixture was concentrated, giving 1.2 g of product having a melting point of 198–202° C.

b) A solution of 0.7 g (2.3 mmol) of (±)-trans-N-[3,6-dihydroxy-2,2-dimethyl)chroman-4-yl]-N-methylmethanesulfonamide in 8 ml of DMF was added dropwise to a solution of 64 mg (2.7 mmol) of 80 percent sodium hydride in 6 ml of DMF. After one hour, 0.56 g (2.4 mmol) of 4,4,4-trifluorobutyl iodide was added, and the mixture was stirred at RT overnight. The reaction mixture was concentrated under reduced pressure and the residue was extracted with EA and water and purified by silica gel chromatography, giving 0.71 g of (±)-trans-N-[3-hydroxy-2,2-dimethyl-6-(4,4,4-trifluorobutoxy)chroman-4-yl]-N-methyl-methanesulfonamide; m.p. 161–163° C.

EXAMPLE 14
(±)-trans-N-(6-Butoxy-3-hydroxy-2,2-dimethylchroman-4-yl)-N-ethyl-methanesulfonamide

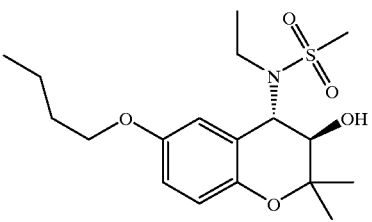

The compound was obtained from 6-butoxy-2,2-dimethyl-3,4-epoxychroman (Example 5d) and ethyl-methanesulfonamide similarly to Example 5e. After silica gel chromatography using methylene chloride/methanol 97:3, the title compound of a melting point of 139–140° C. was isolated.

EXAMPLE 15
N-(6-Butoxy-2,2-dimethyl-2H-chromen-4-yl)-N-ethyl-methanesulfonamide

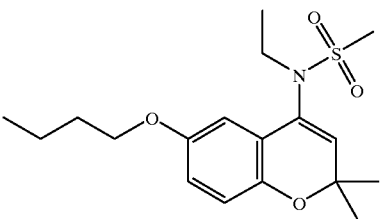

The compound was formed as a by-product in the preparation of the compound of Example 14 and was isolated during the chromatography mentioned therein as the least polar fraction. m.p. 68–70° C.

EXAMPLE 16
(3S, 4R)-(−)-N-(6-Butoxy-3-hydroxy-2,2-dimethylchroman-4-yl)-N-methyl-methanesulfonamide

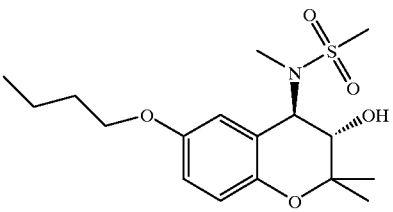

a) (3S, 4S)-(−)-6-Butoxy-2,2-dimethyl-3,4-epoxychroman At 0° C., 76 ml (42 mmol) of a 0.55 M sodium hypochlorite solution which had been adjusted to pH 11.3 using disodium hydrogen phosphate were added to a solution of 4.6 g (20 mmol) of 6-butoxy-2,2-dimethyl-2H-chromen (Example 5b) and 0.5 g (0.8 mmol) of (S,S)-(+)-N,N'-bis-(3,5-di-tert-butylsalicylidene)-1,2-diaminocyclohexanemanganese(III) chloride (Jacobsen's catalyst) in 20 ml of methylene chloride. The reaction mixture was stirred vigorously for 3 h and the organic phase was then separated off and the aqueous phase was extracted twice with methylene chloride. Silica gel chromatography of the crude product using cyclohexane/EA 9:1 gave 1.6 g of (3S, 4S)-(−)-6-butoxy-2,2-dimethyl-3,4-epoxychroman; optical rotation −14.9° (c=0.6; methanol).

b) Similarly to Example 5e, 1 g of (3S, 4S)-(−)-6-butoxy-2,2-dimethyl-3,4-epoxychroman gave 0.7 g of (3S, 4R)-(−)-N-(6-butoxy-3-hydroxy-2,2-dimethylchroman-4-yl)-N-methyl-methanesulfonamide; m.p. 152–154° C.; optical rotation −9.9 (c=0.5; methanol).

EXAMPLE 17
(3S, 4R)-(−)-N-(6-Benzyloxy-3-hydroxy-2,2-dimethylchroman-4-yl)-N-methyl-ethanesulfonamide

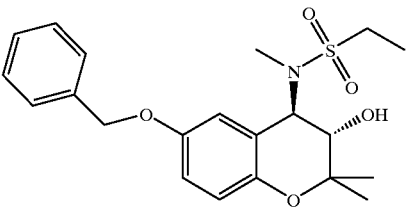

a) (3S, 4S)-6-Benzyloxy-2,2-dimethyl-3,4-epoxychroman
Similarly to Example 16a, 5.0 g of 6-benzyloxy-2,2-dimethyl-2H-chromen (Example 1d) gave 2.3 g of the chiral epoxide.

b) A mixture of 1.0 g (37 mmol) of (3S, 4S)-6-benzyloxy-2,2-dimethyl-3,4-epoxychroman, 1.45 g (74 mmol) of N-methyl-N-trimethylsilyl-ethanesulfonamide and 1.17 g of tetrabutylammonium fluoride trihydrate (37 mmol) in 5 ml of THF was heated at 60° C. for 15 h. The solvent was distilled off, and the residue was then separated over a silica gel column and the product was recrystallized from isopropanol. This gave 0.4 g of (3S, 4R)-(+)-N-(6-benzyloxy-3-hydroxy-2,2-dimethylchroman-4-yl)-N-methyl-ethanesulfonamide; m.p. 172–174° C.; optical rotation −40.8°.

EXAMPLE 18
(3R, 4S)-(+)-N-[-3-Hydroxy-2,2-dimethyl-6-(4,4,4-trifluorobutoxy)chroman-4-yl]-N-methyl-ethanesulfonamide

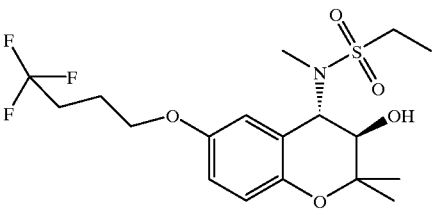

a) Similarly to Example 17 a, but using (R,R)-(+)-N,N'-bis-(3,5-di-tert-butylsalicylidene)-1,2-diaminocyclohexanemanganese(III) chloride, (3R, 4R)-6-benzyloxy-2,2-dimethyl-3,4-epoxychroman was obtained.

b) (3R, 4S)-(+)-N-(6-Benzyloxy-3-hydroxy-2,2-dimethylchroman-4-yl)-N-methyl-ethanesulfonamide A solution of 3.7 g (13 mmol) of (3R, 4R)-6-benzyloxy-2,2-dimethyl-3,4-epoxychroman in 6.5 ml of DMSO was added to a solution of 2.1 g (17 mmol) of N-methyl-ethanesulfonamide and 0.2 g (6.7 mmol) of 80% sodium hydride in 6.5 ml of DMSO, and the mixture was heated at 60° C. for 20 h. The reaction mixture was poured into 300 ml of water and the precipitated product was filtered off with suction. Purification by silica gel chromatography using cyclohexane/EA 8:2 gave 1.9 g of (3R, 4S)-(+)-N-(6-benzyloxy-3-hydroxy-2,2-dimethylchroman-4-yl)-N-methyl-ethanesulfonamide; m.p. 165–167° C.

c) (3R, 4S)-(+)-N-(3,6-Dihydroxy-2,2-dimethylchroman-4-yl)-N-methyl-ethanesulfonamide Similarly to Example 13 a, 1.7 g of the above benzyl ether gave, after hydrogenation, 1.3 g of the title compound.

d) Similarly to Example 13 b, 1.15 g of (3R, 4S)-(+)-N-(3,6-dihydroxy-2,2-dimethylchroman-4-yl)-N-methyl-ethanesulfonamide gave, by alkylation with 4,4,4-trifluorobutyl iodide, 1.1 g of (3R, 4S)-(+)-N-[3-hydroxy-2,2-dimethyl-6-(4,4,4-trifluorobutoxy)chroman-4-yl]-N-methyl-ethanesulfonamide; m.p. 173–174° C., optical rotation +20.°9.

EXAMPLE 19
(3R,4S)-(+)-N-[3-Hydroxy-2,2-dimethyl-6-(4,4,4-trifluorobutoxy)chroman-4-yl]-N-methyl-methanesulfonamide

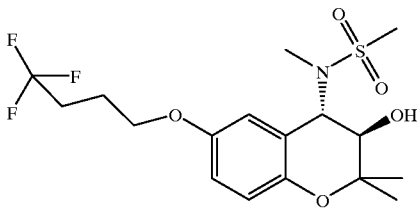

a) 6-(4,4,4-Trifluorobutoxy)-2,2,-dimethylchroman-4-one A solution of 13.4 g (70 mmol) of 2,2-dimethyl-6-hydroxychroman-4-one (Example 1a) in 250 ml of DMF was added dropwise to a solution of 2.65 g (88 mmol) of 80 percent sodium hydride in 170 ml of DMF. The mixture was stirred at RT for 1 h, 14.6 g (76 mmol) of 4,4,4-trifluorobutyl bromide were added and the mixture was left to stand at RT overnight. The reaction mixture was poured into 3 l of water and left to stand overnight. The precipitated product was filtered off with suction, washed with water and dried under reduced pressure. This procedure gave 20.0 g of 6-(4,4,4-trifluorobutoxy)-2,2-dimethylchroman-4-one.

b) 6-(4,4,4-Trifluorobutoxy)-2,2-dimethylchroman-4-ol A solution of 20 g (66 mmol) of 6-(4,4,4-trifluorobutoxy)-2,2-dimethylchroman-4-one and 2.5 g (66 mmol) of sodium borohydride in 100 ml of methanol was stirred at RT overnight. The reaction mixture was poured into ice-water, and mixed with common salt and extracted 4 times with EA. Drying and concentration of the organic phase gave 19.5 g of 6-(4,4,4-trifluorobutoxy)-2,2-dimethylchroman-4-ol.

c) 6-(4,4,4-Trifluorobutoxy)-2,2-dimethyl-2H-chromen A solution of 19.5 g (64 mmol) of 6-(4,4,4-trifluorobutoxy)-2,2-dimethylchroman-4-ol in 200 ml of toluene was admixed with 0.2 g of p-toluenesulfonic acid monohydrate and heated at 100° C. for 2½ h. After cooling, the batch was extracted 2 times with 120 ml of sodium bicarbonate solution each time and stirred with activated carbon. Filtration and concentration under reduced pressure gave 16.7 g of 6-(4,4,4-trifluorobutoxy)-2,2-d imethyl-2H-chromen.

d) (3R,4R)-6-(4,4,4-Trifluorobutoxy)-2,2-dimethyl-3,4-epoxychroman At 0° C., 38.5 ml (22 mmol) of a 0.55 M sodium hypochlorite solution which had been adjusted to pH 11.3 using disodium hydrogen phosphate were added dropwise to a solution of 2.86 g (10 mmol) of 6-(4,4,4-trifluorobutoxy)-2,2-dimethyl-2H-chromen and 0.26 g (0.4 mmol) of (R,R)-(–)-N,N'-bis-(3,5-di-tert-butylsalicylidene)-1,2-diaminocyclohexanemanganese(III) chloride (Jacobsen's catalyst) in 11 ml of methylene chloride. The reaction mixture was stirred vigorously for 1 h, and the organic phase was then separated off and the aqueous phase was extracted once more with a little methylene chloride. To remove the catalyst, the organic phase was filtered through a short silica gel column, and the appropriate fractions were concentrated under reduced pressure. This gave 1.65 g of (3R,4R)-(+)-6-(4,4,4-trifluorobutoxy)-2,2-dimethyl-3,4-epoxychroman as a waxy solid; optical rotation about +13° (c=0.5; methanol).

e) Under argon, 0.77 g (7.1 mmol) of N-methyl-methanesulfonamide was added to a suspension of 0.065 g (2.7 mmol) of 80 percent sodium hydride in 3 ml of DMSO, and the mixture was stirred at RT for 20 min. 1.65 g (5.5 mmol) of (3R,4R)-(+)-6-(4,4,4-trifluorobutoxy)-2,2-dimethyl-3,4-epoxychroman, dissolved in 5 ml of DMSO, were then added dropwise and the batch was left to stand at RT for 4 days and then heated at 45° C. for a further 9 h. The mixture was subsequently poured into water and the precipitate was filtered off with suction and dried thoroughly under reduced pressure, giving 1.9 g of (3R,4S)-(+)-[3-hydroxy-2,2-dimethyl-6-(4,4,4-trifluorobutoxy)chroman-4-yl]-N-methyl-methanesulfonamide, which was recrystallized from a little isopropanol (–>1.4 g; m.p. 178–179° C.; optical purity (chiral HPLC) 100%).

EXAMPLE 20
(3S,4R)-(–)-N-[3-Hydroxy-2,2-dimethyl-6-(4,4,4-trifluorobutoxy)chroman-4-yl]-N-methyl-methanesulfonamide

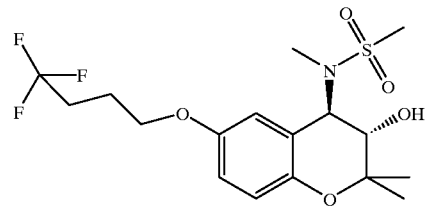

The compound was obtained similarly to Example 19, but using (S,S)-(–)-N,N'-bis-(3,5-di-tert-butylsalicylidene)-1,2-diaminocyclohexanemanganese(III) chloride as epoxidation catalyst. m.p. 179° C.; optical purity (chiral HPLC) 100%.

EXAMPLE 21
(±)-trans-N-[3-Acetoxy-6-(4,4,4-trifluorobutoxy)-2,2-dimethylchroman-4-yl]-N-methyl-methanesulfonamide

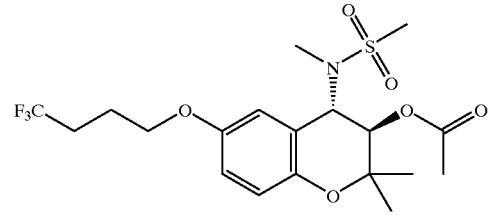

Similar to Example 2, 3.5 g of (±)-trans-N-[3-hydroxy-2,2-dimethyl-6-(4,4,4-trifluorobutoxy)-chroman-4-yl]-N- methyl-methanesulfonamide (example 13) and 28 ml of acetic anhydride in 55 ml of pyridine gave 3.7 g of (±)-trans-N-[3-acetoxy-6-(4,4,4-trifluorobutoxy)-2,2-dimethylchroman-4-yl]-N-methyl-methanesulfonamide; m.p. 106° C.

EXAMPLE 22

N-[6-(4,4,4-Trifluorobutoxy)-2,2-dimethyl-2H-chromen-4-yl]-N-methyl-methanesulfonamide

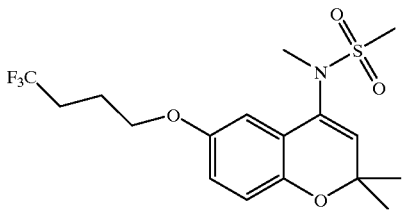

A solution of 3.5 g of (±)-trans-N-[3-acetoxy-6-(4,4,4-trifluorobutoxy)-2,2-dimethylchroman-4-yl]-N-methyl-methanesulfonamide (example 21) and 6.8 g of DBU in 30 ml of toluene was heated at 105° C. for 20 h. The reaction mixture was diluted with EA and washed with hydrochloric acid until the aqueous phase gave an acidic reaction. The mixture was washed with sodium bicarbonate solution, dried over magnesium sulfate, concentrated i. vac. and triturated with heptane, giving 1.7 g N-[6-( 4,4,4-trifluorobutoxy)-2,2-dimethyl-2H-chromen-4-yl]-N-methyl-methanesulfonamide; m.p. 118° C.

EXAMPLE 23

(3R,4S)-{[3-Hydroxy-2,2-dimethyl-6-(4,4,4-trifluoro-butoxy)-chroman-4-yl]-methanesulfonyl-amino}-acetic acid methyl ester

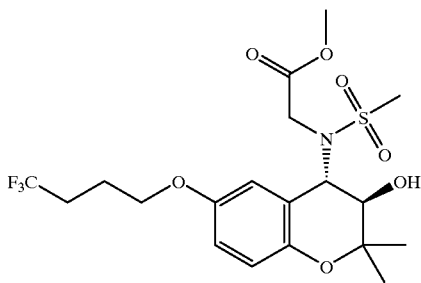

a) (3R,4S)- N-[3-Hydroxy-2,2-dimethyl-6-(4,4,4-trifluoro-butoxy)-chroman-4-yl]-methanesulfonamide
Under argon, 0.82 g (8.6 mmol) of methanesulfonamide was added to a suspension of 0.2 g (6.6 mmol) of 80 percent sodium hydride in 3.5 ml of DMSO, and the mixture was stirred at RT for 30 min. 2.0 g (6.6 mmol) of (3R,4R)-(+)-6-(4,4,4-trifluorobutoxy)-2,2-dimethyl-3,4-epoxychroman (example 19d), dissolved in 6 ml of DMSO, were then added dropwise and the batch was heated at 60° C. for 20 h. The mixture was subsequently poured into water and the precipitate was filtered off with suction and dried thoroughly under reduced pressure, giving 1.6 g of (3R,4S)- N-[3-hydroxy-2,2-dimethyl-6-(4,4,4-trifluoro-butoxy)-chroman-4-yl]-methanesulfonamide; m.p. 186° C.

b) A solution of 0.5 g (1.3 mmol) of the above compound and 0.05 g (1.7 mmol) of 80 percent sodium hydride in 5 ml of DMF was stirred at RT for 1 h. 0.2 g (1.3 mmol) of methyl bromoacetate was then added, and the batch was stirred at RT overnight. After work up and purification by silica gel chromatography 0.2 g of (3R,4S)-{[3-hydroxy-2,2-dimethyl-6-(4,4,4-trifluoro-butoxy)-chroman-4-yl]-methanesulfonyl-amino}-acetic acid methyl ester were obtained.

EXAMPLE 24

Analogous to the methods described above the following compounds can be prepared and are of specific significance:

a) trans-N-[3-Hydroxy-2,2-dimethyl-6-(4,4,4-trifluorobutoxy)chroman-4-yl]-N-ethyl-methanesulfonamide;

b) trans-N-[3-Hydroxy-2,2-dimethyl-6-(4,4,4-trifluorobutoxy)chroman-4-yl]-N-(2,2,2-trifluoroethyl)-methanesulfonamide;

c) trans-N-[3-Hydroxy-2,2-dimethyl-6-(4,4,4-trifluorobutoxy)chroman4-yl]-N-propyl-methanesulfonamide;

d) trans-N-[3-Hydroxy-2,2-dimethyl-6-(4,4,4-trifluorobutoxy)chroman-4-yl]-N-ethyl-ethanesulfonamide;

e) trans-N-[3-Hydroxy-2,2-dimethyl-6-(4,4,4-trifluorobutoxy)chroman-4-yl]-N-(2,2,2-trifluoroethyl)-ethanesulfonamide;

f) trans-N-[3-Hydroxy-2,2-dimethyl-6-(4,4,4-trifluorobutoxy)chroman-4-yl]-N-propyl-ethanesulfonamide;

g) trans-N-[3-Hydroxy-2,2-dimethyl-6-(3,3,3-trifluoropropoxy)chroman-4-yl]-N-methyl-methanesulfonamide;

h) trans-N-[3-Hydroxy-2,2-dimethyl-6-(3,3,3-trifluoropropoxy)chroman-4-yl]-N-ethyl-methanesulfonamide;

i) trans-N-[3-Hydroxy-2,2-dimethyl-6-(cyclopropylmethoxy)chroman-4-yl]-N-methyl-methanesulfonamide;

j) trans-N-[3-Hydroxy-2,2-dimethyl-6-(cyclopropylmethoxy)chroman-4-yl]-N-methyl-ethanesulfonamide.

Pharmacological Investigations $I_{sK}$ channels from man, rat or guinea-pig were expressed in Xenopus oocytes. To do this, oocytes were first isolated from Xenopus laevis and defolliculated. $I_{sK}$-encoding RNA synthesized in vitro was then injected into these oocytes. After $I_{sK}$ protein expression for 2–8 days, $I_{sK}$ currents were measured in the oocytes using the two microelectrode voltage clamp technique. The $I_{sK}$ channels were in this case as a rule activated using voltage jumps to −10 mV lasting 15 s. The bath was irrigated with a solution of the following composition: NaCl 96 mM, KCl 2 mM, $CaCl_2$ 1.8 mM, $MgCl_2$ 1 mM, HEPES 5 mM (titrated with NaOH to pH 7.5). These experiments were carried out at room temperature. The following were employed for acquiring data and analysis: Geneclamp amplifier (Axon Instruments, Foster City, USA) and MacLab D/A converter and software (ADlnstruments, Castle Hill, Australia). The substances according to the invention were tested by adding them to the bath solution in different concentrations. The effects of the substances were calculated as the percentage inhibition of the $I_{sK}$ control current, which was obtained when no substance was added to the solution. The data were then extrapolated using the Hill equation in order to determine the inhibitory concentrations $IC_{50}$ for the respective substances.

References: A. E. Busch, H.-G. Kopp, S. Waldegger, I. Samarzija, H. Süßbrich, G. Raber, K. Kunzelmann, J. P. Ruppersberg and F. Lang; "Inhibition of both exogenously expressed $I_{sK}$ and endogenous $K^+$ channels in Xenopus oocytes by isosorbide dinitrate"; J. Physiol. 491 (1995), 735–741; T. Takumi, H. Ohkubo and S. Nakanishi; "Cloning of a membrane protein that induces a slow voltage-gated potassium current"; Science 242 (1989), 1042–1045; M. D. Varnum, A. E. Busch, C. T. Bond, J. Maylie and J. P. Adelman; "The mink channel underlies the cardiac potassium current and mediates species-specific responses to protein kinase"; C. Proc. Natl. Acad. Sci. SA 90 (1993), 11528–11532.

In the described manner, using the human $I_{sK}$ protein, the following $IC_{50}$ values were determined for the compounds according to the invention:

| Compound | IC-50 [μM] |
|---|---|
| Example 1 | 0.2 |
| Example 2 | 13 |
| Example 3 | 6.5 |
| Example 4 | 1.6 |
| Example 5 | 0.25 |
| Example 6 | >10 |
| Example 7 | 1.6 |
| Example 8 | 0.9 |
| Example 9 | 2.6 |
| Example 10 | 0.4 |
| Example 11 | 1.6 |
| Example 12 | 0.8 |
| Example 13 | 0.2 |
| Example 14 | 0.2 |
| Example 15 | 1.3 |
| Example 16 | 0.4 |
| Example 17 | 0.4 |
| Example 18 | 0.1 |
| Example 19 | 0.1 |
| Example 20 | 0.4 |
| Example 21 | ~10 |
| Example 22 | 0.6 |
| Example 23a | 1.7 |

The foregoing written description relates to various embodiments of the present invention. Numerous changes and modifications may be made therein without departing from the spirit and scope of the invention as defined in the following claims.

What is claimed is:

1. A compound of the formula I, in which R(5) is attached to one of the positions labeled 5, 6, 7 and 8 and in which:

R(1) and R(2)
independently of one another are hydrogen, $CF_3$, $C_2F_5$, $C_3F_7$, alkyl having 1, 2, 3, 4, 5 or 6 carbon atoms or phenyl,
which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino; or
R(1) and R(2)
together are an alkylene chain having 2, 3, 4, 5, 6, 7, 8, 9 or 10 carbon atoms;

R(3) is R(10)—$C_nH_{2n}$—NR(11)— or R(10)—$C_nH_{2n}$—,
where one $CH_2$ group in the group $C_nH_{2n}$ is $CH_2$ or is replaced by —O—, —CO—, —S—, —SO—, —$SO_2$— or —NR(12a)—;
R(12a) is hydrogen, methyl or ethyl;
R(10) is hydrogen, methyl, cycloalkyl having 3, 4, 5, 6, 7 or 8 carbon atoms, $CF_3$, $C_2F_5$ or $C_3F_7$;
n is zero, 1, 2, 3, 4, 5, 6, 7, 8, 9 or 10;
R(11) is hydrogen or alkyl having 1, 2, 3, 4, 5 or 6 carbon atoms; or
R(10) and R(11)
together are a bond, if n is not less than 3; or
R(3) together with R(4)
is an alkylene chain having 3, 4, 5, 6, 7 or 8 carbon atoms,
where a $CH_2$ group of the alkylene chain is $CH_2$ or is replaced by —O—, —CO—, —S—, —SO—, —$SO_2$— or —NR(12a)—;
R(12a) is hydrogen, methyl or ethyl;
R(4) is R(13)—$C_rH_{2r}$—,
where a $CH_2$ group of the group $C_rH_{2r}$ is $CH_2$ or is replaced by —O—, —CH=CH—, —C≡C—, —CO—, —CO—O—, —O—CO—, —S—, —SO—, —$SO_2$— or —NR(14)—;
R(14) is hydrogen or alkyl having 1, 2 or 3 carbon atoms;
R(13) is $CH_3$, $CF_3$, $C_2F_5$, $C_3F_7$, cycloalkyl having 3, 4, 5, 6, 7 or 8 carbon atoms, NR(15)R(16), phenyl or a nitrogen-containing heterocycle having 1, 2, 3, 4, 5, 6, 7, 8 or 9 carbon atoms,
where phenyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(15) and R(16)
together are a chain of 4 or 5 methylene groups of which one methylene group is $CH_2$ or is replaced by —O—, —S—, —NH—, —N(methyl)— or —N(benzyl)—;
r is zero, 1, 2, 3, 4, 5, 6, 7, 8, 9, 10, 11, 12, 13, 14, 15, 16, 17, 18, 19 or 20;
R(5) is —Y—$C_sH_{2s}$—R(18) or phenyl,
which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
Y is —O—, —S— or —NR(10c)—; R(10c) is hydrogen or alkyl having 1, 2 or 3 carbon atoms;
s is 1, 2, 3, 4, 5, 6, 7 or 8;
R(18) is hydrogen, $CF_3$, $C_2F_5$, $C_3F_7$, cycloalkyl having 3, 4, 5, 6, 7 or 8 carbon atoms, —COOR(21), NR(15a)R(16a), an unsubstituted nitrogen-containing heterocycle having 1, 2, 3, 4, 5, 6, 7, 8 or 9 carbon atoms, phenyl or thienyl,
where phenyl and thienyl are unsubstituted or substituted by 1 or 2 substituents selected from the group consisting of F, Cl, Br, I, $CF_3$, methyl, methoxy, sulfamoyl, methylsulfonyl and methylsulfonylamino;
R(15a) and R(16a)
together are a chain of 4 or 5 methylene groups of which one methylene group is $CH_2$ or is replaced by —O—, —S—, —NH—, —N(methyl)— or —N(benzyl)—;

R(21) is hydrogen or alkyl having 1, 2 or 3 carbon atoms;
R(6) is OR(10d) or OCOR(10d); R(10d) is hydrogen or alkyl having 1, 2 or 3 carbon atoms;
B is hydrogen; or
R(6) and B
together are a bond; or a physiologically tolerable salt thereof.

2. A compound of the formula I as claimed in claim 1 in which:
R(1) and R(2)
independently of one another are hydrogen, $CF_3$, $C_2F_5$, $C_3F_7$ or alkyl having 1, 2, 3, 4, 5 or 6 carbon atoms; or
R(1) and R(2)
together are an alkylene chain having 2, 3, 4, 5, 6, 7, 8, 9 or 10 carbon atoms;
R(3) is R(10)—$C_nH_{2n}$;
R(10) is methyl, $CF_3$, $C_2F_5$ or $C_3F_7$;
n is zero, 1, 2, 3, 4, 5 or 6;
R(4) is R(13)—$C_rH_{2r}$,
where one $CH_2$ group of the group $C_rH_{2r}$ is $CH_2$ or is replaced by —O—, —CH=CH—, —C≡C—, —CO—, —CO—O—, —O—CO—, —S—, —SO—, —$SO_2$— or —NR(14)—;
R(14) is hydrogen or alkyl having 1, 2 or 3 carbon atoms;
R(13) is $CH_3$, $CF_3$, $C_2F_5$, $C_3F_7$, cycloalkyl having 3, 4, 5, 6, 7 or 8 carbon atoms, NR(15)R(16), phenyl or a nitrogen-containing heterocycle having 1, 2, 3, 4, 5, 6, 7, 8 or 9 carbon atoms,
where phenyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(15) and R(16)
together are a chain of 4 or 5 methylene groups of which one methylene group is $CH_2$ or is replaced by —O—, —S—, —NH—, —N(methyl)— or —N(benzyl)—;
r is zero, 1, 2, 3, 4, 5, 6, 7, 8, 9, 10, 11 or 12;
R(5) is —Y—$C_sH_{2s}$—R(18) or phenyl,
which is unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
Y is —O— or —S—;
s is 1, 2, 3, 4, 5, 6, 7 or 8;
R(18) is hydrogen, $CF_3$, $C_2F_5$, $C_3F_7$, cycloalkyl having 3, 4, 5, 6, 7 or 8 carbon atoms, —COOR(21), NR(15a)R(16a), an unsubstituted nitrogen-containing heterocycle having 1, 2, 3, 4, 5, 6, 7, 8 or 9 carbon atoms, phenyl or thienyl,
where phenyl and thienyl are unsubstituted or substituted by 1 or 2 substituents selected from the group consisting of F, Cl, Br, I, $CF_3$, methyl, methoxy, sulfamoyl, methylsulfonyl and methylsulfonylamino;
R(15a) and R(16a) together are a chain of 4 or 5 methylene groups of which one methylene group is $CH_2$ or is replaced by —O—, —S—, —NH—, —N(methyl)— or —N(benzyl)—;
R(21) is alkyl having 1, 2 or 3 carbon atoms;

R(6) is OR(10d) or OCOR(10d);
R(10d) is hydrogen or alkyl having 1, 2 or 3 carbon atoms;
B is hydrogen; or
R(6) and B together are a bond; or a physiologically tolerable salt thereof.

3. A compound of the formula I as claimed in claim 2, in which R(5) is attached to the position labeled 6. and is a compound of the formula Ia,

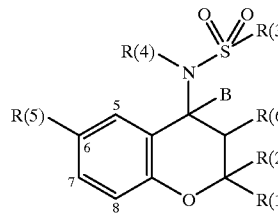

in which the radicals R(1), R(2), R(3), R(4), R(5), R(6) and B are as defined in claim 2; or a physiologically tolerable salt thereof.

4. A compound of the formula Ia as claimed in claim 3, in which:
R(1) and R(2)
independently of one another are hydrogen, $CF_3$ or alkyl having 1, 2 or 3 carbon atoms; or
R(1) and R(2)
together are an alkylene chain having 2, 3, 4, 5 or 6 carbon atoms;
R(3) is R(10)—$C_nH_{2n}$;
R(10) is methyl or $CF_3$;
n is zero, 1 or 2;
R(4) is R(13)—$C_rH_{2r}$,
where a $CH_2$ group of the group $C_rH_{2r}$ is $CH_2$ or is replaced by —O—, —CO—, —CO—O—, —O—CO—, —S—, —SO—, —$SO_2$— or —NR(14)—;
R(14) is hydrogen or alkyl having 1, 2 or 3 carbon atoms;
R(13) is $CH_3$, $CF_3$, NR(15)R(16), phenyl or a nitrogen-containing heterocycle having 1, 2, 3, 4, 5, 6, 7, 8 or 9 carbon atoms,
where phenyl and the nitrogen-containing heterocycle are unsubstituted or substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(15) and R(16)
together are a chain of 4 or 5 methylene groups of which one methylene group is $CH_2$ or is replaced by —O—, —S—, —NH—, —N(methyl)— or —N(benzyl)—;
r is zero, 1, 2, 3, 4, 5, 6, 7 or 8;
R(5) is —Y—$C_sH_{2s}$—R(18);
Y is —O—;
s is 1, 2, 3, 4, 5 or 6;
R(18) is hydrogen, $CF_3$, —COOR(21), NR(15a)R(16a), an unsubstituted nitrogen-containing heterocycle having 1, 2, 3, 4, 5, 6, 7, 8 or 9 carbon atoms, phenyl or thienyl,
where phenyl and thienyl are unsubstituted or substituted by 1 or 2 substituents selected from the group consisting of F, Cl, Br, I, CF₃, methyl, methoxy, sulfamoyl, methylsulfonyl and methylsulfonylamino;

R(15a) and R(16a)
together are a chain of 4 or 5 methylene groups of which one CH₂ group is CH₂ or is replaced by —O—, —S—, —NH—, —N(methyl)— or —N(benzyl)—;

R(21) is alkyl having 1, 2 or 3 carbon atoms;

R(6) is OH;

B is hydrogen; or

R(6) and B
together are a bond; or a physiologically tolerable salt thereof.

5. A compound of the formula Ia as claimed in claim 3, in which:

R(1) and R(2)
are methyl;

R(3) is methyl or ethyl;

R(4) is R(13)—C$_r$H$_{2r}$,
where a CH₂ group of the group C$_r$H$_{2r}$ is CH₂ or is replaced by —O—, —CO—, —CO—O— or —O—CO; R(13) is CH₃ or CF₃;

r is zero, 1, 2, 3, 4, 5, 6, 7 or 8;

R(5) is —Y—C$_s$H$_{2s}$—R(18);

Y is —O—;

s is 1, 2, 3, 4, 5 or 6;

R(18) is hydrogen, CF₃, —COOR(21), phenyl or thienyl,
where phenyl and thienyl are unsubstituted or substituted by 1 or 2 substituents selected from the group consisting of F, Cl, Br, CF₃, methyl and methoxy;

R(21) is alkyl having 1, 2 or 3 carbon atoms;

R(6) and B
together are a bond; or a physiologically tolerable salt thereof.

6. A compound of the formula Ia as claimed in claim 3, in which:

R(1) and R(2) are methyl;

R(3) is methyl or ethyl;

R(4) is R(13)—C$_r$H$_{2r}$,
where a CH₂ group of the group C$_r$H$_{2r}$ is CH₂ or is replaced by —O—, —CO—, —CO—O— or —O—CO;

R(13) is CH₃ or CF₃;

r is zero, 1, 2, 3, 4, 5, 6, 7 or 8;

R(5) is —Y—C$_s$H$_{2s}$—R(18);

Y is —O—;

s is 1, 2, 3, 4, 5 or 6;

R(18) is hydrogen, CF₃, phenyl or thienyl,
where phenyl and thienyl are unsubstituted or substituted by 1 or 2 substituents selected from the group consisting of F, Cl, Br, CF₃, methyl and methoxy;

R(6) is OH;

B is hydrogen; or a physiologically tolerable salt thereof.

7. A process for preparing a compound of the formula I as claimed in claim 1, which comprises a) reacting a compound of the formula II,

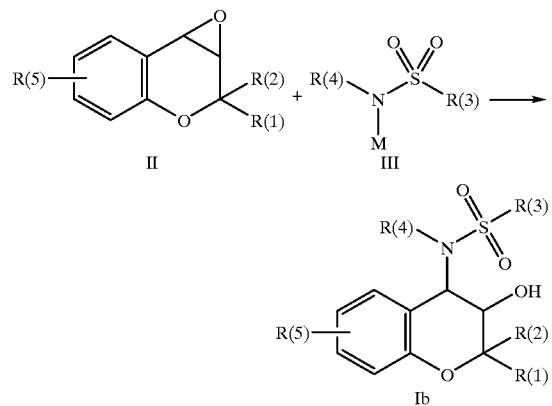

in which R(1), R(2) and R(5) are defined in claim 1 with a sulfonamide of the formula III in which R(3) and R(4) are as defined in claim 1 and M is hydrogen or a metal equivalent or a trialkylsilyl radical to give a chromanol of the formula Ib; or b) reacting a compound of the formula Ib with an alkylating agent of the formula R(10d)-L or an acylating agent of the formula R(10d)-COL or an anhydride of the formula (R(10d)—CO)₂O, in which R(10d) is as defined in claim 1 and L is a nucleofugic leaving group in an alkylation or acylation reaction to give a compound of the formula Ic in which R(6) is OR(10d) or OCOR(10d);

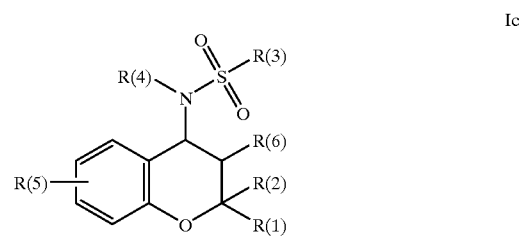

or c) converting a compound of the formula Ic,

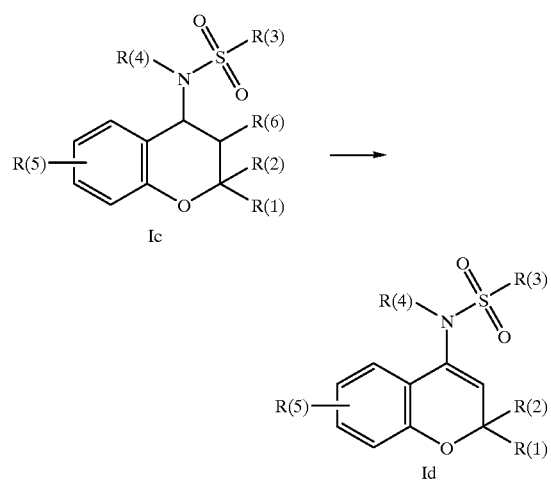

in which R(1), R(2), R(3), R(4) and R(5) are as defined in claim 1 and R(6) is OCOCH₃ in an elimination reaction to give a compound of the formula Id in which R(1), R(2), R(3), R(4) and R(5) are as defined in claim 1.

8. A pharmaceutical composition comprising an effective amount of a compound of the formula I as claimed in claim 1, together with a pharmaceutically acceptable carrier.

9. A pharmaceutical composition as claimed in claim 8 together with one or more other pharmacologically active compounds.

10. A method for the therapeutic treatment and prophylaxis of a $K^+$ channel-mediated disease which comprises administering to a mammal an effective amount of a compound of the formula I as claimed in claim 1.

11. A method for the inhibition of gastric acid secretion which comprises administering to a mammal an effective amount of a compound of the formula I as claimed in claim 1.

12. A method for the therapeutic treatment or prophylaxis of an ulcer of the stomach or of the intestinal region which comprises administering to a mammal an effective amount of a compound of the formula I as claimed in claim 1.

13. A method for the therapeutic treatment or prophylaxis of reflux esophagitis which comprises administering to a mammal an effective amount of a compound of the formula I as claimed in claim 1.

14. A method for the therapeutic treatment or prophylaxis of a diarrheal illness which comprises administering to a mammal an effective amount of a compound of the formula I as claimed in claim 1.

15. A method for the therapeutic treatment or prophylaxis of an arrhythmia which comprises administering to a mammal an effective amount of a compound of the formula I as claimed in claim 1.

16. A method for the therapeutic treatment or prophylaxis of an arrhythmia as claimed in claim 15 wherein the arrhythmia is an atrial, ventricular or supraventricular arrhythmia.

17. A method for the therapeutic treatment or prophylaxis of a cardiac arrhythmia which comprises administering to a mammal an effective amount of a compound of the formula I as claimed in claim 1.

18. A method for the therapeutic treatment or prophylaxis of a cardiac arrhythmia as claimed in claim 17 wherein said cardiac arrhythmia is eliminated by action potential prolongation.

19. A method for the therapeutic treatment or prophylaxis of an atrial fibrillation or an atrial flutter which comprises administering to a mammal an effective amount of a compound of the formula I as claimed in claim 1.

20. A method for the therapeutic treatment or prophylaxis of a reentry arrhythmia which comprises administering to a mammal an effective amount of a compound of the formula I as claimed in claim 1.

21. A method for the prevention of sudden heart death as a result of ventricular fibrillation which comprises administering to a mammal an effective amount of a compound of the formula I as claimed in claim 1.

22. A method for the therapeutic treatment of cardiac insufficiency which comprises administering to a mammal an effective amount of a compound of the formula I as claimed in claim 1.

23. A method for the therapeutic treatment of cardiac insufficiency as claimed in claim 22 wherein the cardiac insufficiency is congestive heart failure.

24. A method for the inhibition of stimulated gastric acid secretion, for the therapy or prophylaxis of an ulcer of the stomach or of the intestinal region, of reflux esophagitis, of a diarrheal illness, for the therapy or prophylaxis of an arrhythmia, of an atrial fibrillation and an atrial flutter and a reentry arrhythmia, or for the prevention of sudden heart death as a result of ventricular fibrillation, which comprises administering to a mammal an effective amount of a compound of the formula I as claimed in claim 1.

25. A pharmaceutical composition comprising an effective amount of a compound of the formula I as claimed in claim 1 and a beta-adrenergic receptor blocker as active compounds, together with a pharmaceutically acceptable carrier.

26. A pharmaceutical composition comprising an effective amount of a compound of the formula Ia as claimed in claim 3, together with a pharmaceutically acceptable carrier.

27. A pharmaceutical composition as claimed in claim 26 together with one or more other pharmacologically active compounds.

28. A method for the therapeutic treatment and prophylaxis of a $K^+$ channel-mediated disease which comprises administering to a mammal an effective amount of a compound of the formula Ia as claimed in claim 3.

29. A method for the inhibition of gastric acid secretion which comprises administering to a mammal an effective amount of a compound of the formula Ia as claimed in claim 3.

30. A method for the therapeutic treatment or prophylaxis of an ulcer of the stomach or of the intestinal region which comprises administering to a mammal an effective amount of a compound of the formula Ia as claimed in claim 3.

31. A method for the therapeutic treatment or prophylaxis of reflux esophagitis which comprises administering to a mammal an effective amount of a compound of the formula Ia as claimed in claim 3.

32. A method for the therapeutic treatment or prophylaxis of a diarrheal illness which comprises administering to a mammal an effective amount of a compound of the formula Ia as claimed in claim 3.

33. A method for the therapeutic treatment or prophylaxis of an arrhythmia which comprises administering to a mammal an effective amount of a compound of the formula Ia as claimed in claim 3.

34. A method for the therapeutic treatment or prophylaxis of an arrhythmia as claimed in claim 33 wherein said arrhythmia is an atrial, ventricular or supraventricular arrhythmia.

35. A method for the therapeutic treatment or prophylaxis of a cardiac arrhythmia which comprises administering to a mammal an effective amount of a compound of the formula Ia as claimed in claim 3.

36. A method for the therapeutic treatment or prophylaxis of a cardiac arrhythmia as claimed in claim 35 wherein said cardiac arrhythmia is eliminated by action potential prolongation.

37. A method for the therapeutic treatment or prophylaxis of an atrial fibrillation or an atrial flutter which comprises administering to a mammal an effective amount of a compound of the formula Ia as claimed in claim 3.

38. A method for the therapeutic treatment or prophylaxis of a reentry arrhythmia which comprises administering to a mammal an effective amount of a compound of the formula Ia as claimed in claim 3.

39. A method for the prevention of sudden heart death as a result of ventricular fibrillation which comprises administering to a mammal an effective amount of a compound of the formula Ia as claimed in claim 3.

40. A method for the therapeutic treatment of a cardiac insufficiency which comprises administering to a mammal an effective amount of a compound of the formula Ia as claimed in claim 3.

41. A method for the therapeutic treatment of a cardiac insufficiency as claimed in claim 40 wherein the cardiac insufficiency is congestive heart failure.

42. A method for the inhibition of stimulated gastric acid secretion, for the therapy or prophylaxis of an ulcer of the stomach or of the intestinal region, of reflux esophagitis, of a diarrheal illness, for the therapy or prophylaxis of an arrhythmia, of an atrial fibrillation and an atrial flutter and a reentry arrhythmia, or for the prevention of sudden heart death as a result of ventricular fibrillation, which comprises administering to a mammal an effective amount of a compound of the formula Ia as claimed in claim 3.

43. A pharmaceutical composition comprising an effective amount of a compound of the formula Ia as claimed in claim 3 and a beta-adrenergic receptor blocker as active compounds, together with a pharmaceutically acceptable carrier.

* * * * *